(12) United States Patent
Ehlert et al.

(10) Patent No.: US 9,239,036 B2
(45) **Date of Patent: *Jan. 19, 2016**

(54) ULTRASONIC LIQUID TREATMENT AND DELIVERY SYSTEM AND PROCESS

(75) Inventors: Thomas David Ehlert, Neenah, WI (US); Patrick Sean McNichols, Hortonville, WI (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 931 days.

This patent is subject to a terminal disclaimer.

(21) Appl. No.: 12/438,315

(22) PCT Filed: Sep. 7, 2007

(86) PCT No.: PCT/IB2007/053622

§ 371 (c)(1), (2), (4) Date: Oct. 30, 2009

(87) PCT Pub. No.: WO2008/047259

PCT Pub. Date: Apr. 24, 2008

(65) Prior Publication Data

US 2010/0044452 A1 Feb. 25, 2010
US 2013/0214055 A9 Aug. 22, 2013

Related U.S. Application Data

(63) Continuation-in-part of application No. 11/780,860, filed on Jul. 20, 2007, now Pat. No. 7,810,743, and a continuation-in-part of application No. 11/530,311, filed on Sep. 8, 2006, now Pat. No. 7,703,698.

(51) Int. Cl.

| | |
|---|---|
| ***B05B 1/08*** | (2006.01) |
| ***F02M 69/04*** | (2006.01) |

(Continued)

(52) U.S. Cl.
CPC ............ *F02M 69/041* (2013.01); *A61K 9/0024* (2013.01); *F02M 47/027* (2013.01);
(Continued)

(58) Field of Classification Search
USPC ............ 239/4, 102.1, 102.2, 584; 251/129.06
See application file for complete search history.

(56) References Cited

U.S. PATENT DOCUMENTS

| | | | |
|---|---|---|---|
| 2,115,056 | A | 4/1938 | Wynn |
| 2,307,206 | A | 1/1943 | Fischer |

(Continued)

FOREIGN PATENT DOCUMENTS

| | | |
|---|---|---|
| CA | 2175065 | 5/1995 |
| CN | 657067 | 8/1986 |

(Continued)

OTHER PUBLICATIONS

Non-final Office action regarding U.S. Appl. No. 11/963,237, dated Jul. 8, 2010.

(Continued)

*Primary Examiner* — Justin Jonaitis
(74) *Attorney, Agent, or Firm* — Armstrong Teasdale LLP

(57) ABSTRACT

In a system and process for ultrasonically treating a liquid and delivering the liquid as a spray of liquid droplets, liquid is directed to flow along a flow path over a first ultrasonic waveguide, with the first ultrasonic waveguide having at least one agitating member extending outward therefrom and into the flow path. The first ultrasonic waveguide and agitating member(s) are excited to agitate the liquid as the liquid flows along the flow path. The liquid is further directed to flow along the flow path over a second waveguide, with the second waveguide having a terminal end adjacent an exit of the flow path. The second ultrasonic waveguide is ultrasonically excited at least at its terminal end to ultrasonically energize the liquid just prior to the liquid exiting the flow path such that the liquid exits the flow path as a spray of liquid droplets.

17 Claims, 16 Drawing Sheets

(51) Int. Cl.
*A61K 9/00* (2006.01)
*F02M 47/02* (2006.01)
*F02M 51/00* (2006.01)
*F02M 51/06* (2006.01)
*F02M 61/16* (2006.01)
*F23D 11/34* (2006.01)

(52) U.S. Cl.
CPC ......... *F02M51/005* (2013.01); *F02M 51/0603* (2013.01); *F02M 61/168* (2013.01); *F23D 11/345* (2013.01); *F02M 2547/003* (2013.01)

(56) References Cited

U.S. PATENT DOCUMENTS

| | | | |
|---|---|---|---|
| 2,584,053 A | 1/1952 | Seavey et al. | |
| 2,615,692 A | 10/1952 | Muller | |
| 2,620,894 A | 12/1952 | Peterson et al. | |
| 2,661,192 A | 12/1953 | Horsley et al. | |
| 2,946,981 A | 7/1960 | O'Neill | |
| 3,066,232 A | 11/1962 | Branson | |
| 3,160,138 A | 12/1964 | Platzman | |
| 3,202,281 A | 8/1965 | Weston | |
| 3,239,998 A | 3/1966 | Carter et al. | |
| 3,246,881 A | 4/1966 | Davidson et al. | |
| 3,249,453 A | 5/1966 | Schnoring et al. | |
| 3,273,631 A | 9/1966 | Neuman | |
| 3,275,787 A | 9/1966 | Newberry | |
| 3,278,165 A | 10/1966 | Gaffney | |
| 3,284,991 A | 11/1966 | Ploeger et al. | |
| 3,325,348 A | 6/1967 | Bennett | |
| 3,326,470 A | 6/1967 | Loudin et al. | |
| 3,338,992 A | 8/1967 | Kinney | |
| 3,341,394 A | 9/1967 | Kinney | |
| 3,425,951 A | 2/1969 | Ishiwata | |
| 3,463,321 A | 8/1969 | VanIngen | |
| 3,479,873 A | 11/1969 | Hermanns | |
| 3,490,584 A | 1/1970 | Balamuth | |
| 3,502,763 A | 3/1970 | Hartman | |
| 3,519,251 A | 7/1970 | Hammitt et al. | |
| 3,542,345 A | 11/1970 | Kuris | |
| 3,542,615 A | 11/1970 | Dobo et al. | |
| 3,567,185 A | 3/1971 | Ross et al. | |
| 3,591,946 A | 7/1971 | Loe | |
| 3,664,191 A | 5/1972 | Hermanns | |
| 3,692,618 A | 9/1972 | Dorschner et al. | |
| 3,782,547 A | 1/1974 | Dietert | |
| 3,802,817 A | 4/1974 | Matsuki et al. | |
| 3,865,350 A | 2/1975 | Burtis | |
| 3,873,071 A | 3/1975 | Tatebe | |
| 3,904,392 A | 9/1975 | VanIngen et al. | |
| 4,035,151 A | 7/1977 | Czerny et al. | |
| 4,062,768 A | 12/1977 | Elliot | |
| 4,070,167 A | 1/1978 | Barbee et al. | |
| 4,118,797 A | 10/1978 | Tarpley, Jr. | |
| 4,122,797 A | 10/1978 | Kawamura et al. | |
| 4,168,295 A | 9/1979 | Sawyer | |
| 4,218,221 A | 8/1980 | Cottell | |
| 4,249,986 A | 2/1981 | Obeda | |
| 4,259,021 A | 3/1981 | Goudy, Jr. | |
| 4,260,389 A | 4/1981 | Lister | |
| 4,266,879 A | 5/1981 | McFall | |
| 4,340,563 A | 7/1982 | Appel et al. | |
| 4,372,296 A | 2/1983 | Fahim | |
| 4,398,925 A | 8/1983 | Trinh et al. | |
| 4,425,718 A | 1/1984 | Kawaguchi | |
| 4,511,254 A | 4/1985 | North et al. | |
| 4,556,467 A | 12/1985 | Kuhn | |
| 4,612,016 A | 9/1986 | Jaeger et al. | |
| 4,612,018 A | 9/1986 | Tsuboi et al. | |
| 4,663,220 A | 5/1987 | Wisneski et al. | |
| 4,673,512 A | 6/1987 | Schram | |
| 4,693,879 A | 9/1987 | Yoshimura et al. | |
| 4,699,636 A | 10/1987 | Bofinger et al. | |
| 4,706,509 A | 11/1987 | Riebel | |
| 4,708,878 A | 11/1987 | Hagelauer et al. | |
| 4,726,522 A | 2/1988 | Kokubo et al. | |
| 4,743,361 A | 5/1988 | Schram | |
| 4,848,159 A | 7/1989 | Kennedy et al. | |
| 4,877,516 A | 10/1989 | Schram | |
| 4,879,011 A | 11/1989 | Schram | |
| 4,929,279 A | 5/1990 | Hays | |
| 4,974,780 A * | 12/1990 | Nakamura et al. | 239/102.2 |
| RE33,524 E | 1/1991 | Schram | |
| 4,983,045 A * | 1/1991 | Taniguchi | 366/117 |
| 5,006,266 A | 4/1991 | Schram | |
| 5,026,167 A | 6/1991 | Berliner, III | |
| 5,032,027 A | 7/1991 | Berliner, III | |
| 5,059,249 A | 10/1991 | Hays | |
| 5,096,532 A | 3/1992 | Neuwirth et al. | |
| 5,110,403 A | 5/1992 | Ehlert | |
| 5,122,165 A | 6/1992 | Wang et al. | |
| 5,164,094 A | 11/1992 | Stuckart | |
| 5,169,067 A | 12/1992 | Matsusaka et al. | |
| 5,242,557 A | 9/1993 | Jones et al. | |
| 5,258,413 A | 11/1993 | Isayev | |
| 5,260,243 A | 11/1993 | Dunne et al. | |
| 5,269,297 A | 12/1993 | Weng et al. | |
| 5,326,164 A | 7/1994 | Logan | |
| 5,330,100 A | 7/1994 | Malinowski | |
| 5,335,449 A | 8/1994 | Beatty | |
| 5,372,634 A | 12/1994 | Monahan | |
| 5,373,212 A | 12/1994 | Beau | |
| 5,375,926 A | 12/1994 | Omasa | |
| 5,391,000 A | 2/1995 | Taniguchi | |
| 5,466,722 A | 11/1995 | Stoffer et al. | |
| 5,519,670 A | 5/1996 | Walter | |
| 5,536,921 A | 7/1996 | Hedrick et al. | |
| 5,583,292 A | 12/1996 | Karbach et al. | |
| 5,585,565 A | 12/1996 | Glascock et al. | |
| 5,665,383 A | 9/1997 | Grinstaff et al. | |
| 5,681,457 A | 10/1997 | Mahoney | |
| 5,711,888 A | 1/1998 | Trampler et al. | |
| 5,770,124 A | 6/1998 | Marecki et al. | |
| 5,803,270 A | 9/1998 | Brodeur | |
| 5,810,037 A | 9/1998 | Sasaki et al. | |
| 5,831,166 A | 11/1998 | Kozuka et al. | |
| 5,853,456 A | 12/1998 | Bryan et al. | |
| 5,868,153 A | 2/1999 | Cohen et al. | |
| 5,873,968 A | 2/1999 | Pike et al. | |
| 5,902,489 A | 5/1999 | Yasuda et al. | |
| 5,916,203 A | 6/1999 | Brandon et al. | |
| 5,922,355 A | 7/1999 | Parikh et al. | |
| 5,935,883 A | 8/1999 | Pike | |
| 5,937,906 A | 8/1999 | Kozyuk | |
| 5,964,926 A | 10/1999 | Cohen | |
| 5,979,664 A | 11/1999 | Brodeur | |
| 6,010,592 A | 1/2000 | Jameson et al. | |
| 6,020,277 A | 2/2000 | Jameson | |
| 6,035,897 A | 3/2000 | Kozyuk | |
| 6,053,028 A | 4/2000 | Kraus, Jr. et al. | |
| 6,053,424 A * | 4/2000 | Gipson et al. | 239/102.2 |
| 6,055,859 A | 5/2000 | Kozuka et al. | |
| 6,060,416 A | 5/2000 | Kobata et al. | |
| 6,074,466 A | 6/2000 | Iwasa | |
| 6,090,731 A | 7/2000 | Pike et al. | |
| 6,106,590 A | 8/2000 | Ueno et al. | |
| 6,169,045 B1 | 1/2001 | Pike et al. | |
| 6,200,486 B1 | 3/2001 | Chahine et al. | |
| 6,218,483 B1 | 4/2001 | Muthiah et al. | |
| 6,221,258 B1 | 4/2001 | Feke et al. | |
| 6,254,787 B1 | 7/2001 | Kimura et al. | |
| 6,266,836 B1 | 7/2001 | Gallego Juarez et al. | |
| 6,315,215 B1 | 11/2001 | Gipson et al. | |
| 6,322,240 B1 | 11/2001 | Omasa | |
| 6,332,541 B1 | 12/2001 | Coakley et al. | |
| 6,361,697 B1 | 3/2002 | Coury et al. | |
| 6,368,414 B1 | 4/2002 | Johnson | |
| 6,380,264 B1 | 4/2002 | Jameson et al. | |
| 6,383,301 B1 | 5/2002 | Bell et al. | |
| 6,450,417 B1 | 9/2002 | Gipson et al. | |
| 6,467,350 B1 | 10/2002 | Kaduchak et al. | |
| 6,482,327 B1 | 11/2002 | Mori et al. | |
| 6,506,584 B1 | 1/2003 | Chandler et al. | |

(56) References Cited

U.S. PATENT DOCUMENTS 6,547,903 B1 4/2003 McNichols et al.
6,547,935 B2 4/2003 Scott
6,547,951 B1 4/2003 Maekawa
6,551,607 B1 4/2003 Minerath, III et al.
6,576,042 B2 6/2003 Kraus et al.
6,582,611 B1 6/2003 Kerfoot
6,593,436 B2 7/2003 Austin et al.
6,605,252 B2 8/2003 Omasa
6,620,226 B2 9/2003 Hutton et al.
6,624,100 B1 9/2003 Pike et al.
6,627,265 B2 9/2003 Kutilek
6,648,943 B2 11/2003 Possanza et al.
6,655,826 B1 12/2003 Leanos
6,659,365 B2 12/2003 Gipson et al.
6,676,003 B2 1/2004 Ehlert et al.
6,689,730 B2 2/2004 Hortel et al.
6,739,524 B2 5/2004 Taylor-McCune et al.
6,770,600 B1 8/2004 Lamola et al.
6,817,541 B2 11/2004 Sands et al.
6,818,128 B2 11/2004 Minter
6,837,445 B1 1/2005 Tsai
6,841,921 B2 1/2005 Stegelmann
6,858,181 B2 2/2005 Aoyagi
6,878,288 B2 4/2005 Scott
6,883,724 B2 4/2005 Adiga et al.
6,889,528 B2 5/2005 Sen et al.
6,890,593 B2 5/2005 Tian
6,897,628 B2 5/2005 Gunnerman et al.
6,902,650 B2 6/2005 Park et al.
6,911,153 B2 6/2005 Minter
6,929,750 B2 8/2005 Laurell et al.
6,935,770 B2 8/2005 Schueler
6,936,151 B1 8/2005 Lock et al.
7,018,546 B2 3/2006 Kurihara et al.
7,083,322 B2 8/2006 Moore et al.
7,083,764 B2 8/2006 Scott
7,090,391 B2 8/2006 Taniguchi
7,108,137 B2 9/2006 Lal et al.
7,150,779 B2 12/2006 Meegan, Jr.
7,156,201 B2 1/2007 Peshkovskiy et al.
7,293,909 B2 11/2007 Taniguchi
7,322,431 B2 1/2008 Ratcliff
7,338,551 B2 3/2008 Kozyuk
7,404,666 B2 7/2008 Tessien
7,414,009 B2 8/2008 Tanaka et al.
7,419,519 B2 9/2008 Li et al.
7,424,883 B2 * 9/2008 McNichols et al. .......... 123/490
7,438,875 B2 10/2008 Do et al.
7,465,426 B2 12/2008 Kerherve et al.
7,504,075 B2 3/2009 Marhasin
7,516,664 B2 4/2009 Meier et al.
7,533,830 B1 * 5/2009 Rose ................................ 239/4
7,582,156 B2 9/2009 Tanaka et al.
7,597,277 B2 10/2009 Kawakami et al.
7,673,516 B2 * 3/2010 Janssen et al. .................. 73/592
7,703,698 B2 * 4/2010 Janssen et al. ............. 239/102.2
7,712,353 B2 5/2010 Janssen et al.
7,735,751 B2 * 6/2010 Ehlert et al. ............... 239/102.2
7,780,743 B2 8/2010 Greaves et al.
7,785,674 B2 * 8/2010 Janssen et al. ................ 427/600
7,810,743 B2 * 10/2010 McNichols et al. ....... 239/102.2
7,947,184 B2 * 5/2011 Janssen et al. ........... 210/748.01
8,100,346 B2 * 1/2012 Venkataraghavan et al. .......................... 239/102.2
2001/0040935 A1 11/2001 Case
2002/0036173 A1 3/2002 Feke et al.
2002/0164274 A1 11/2002 Haggett et al.
2003/0042174 A1 3/2003 Austin
2003/0047067 A1 3/2003 Kraus et al.
2003/0048692 A1 3/2003 Cohen et al.
2003/0051989 A1 3/2003 Austin
2003/0061939 A1 4/2003 Hutton et al.
2003/0066899 A1 4/2003 Gipson
2003/0116014 A1 6/2003 Possanza et al.
2003/0143110 A1 7/2003 Kritzler et al.
2003/0194692 A1 10/2003 Purdum
2003/0234173 A1 12/2003 Minter
2004/0022695 A1 2/2004 Simon et al.
2004/0065599 A1 4/2004 Lal et al.
2004/0079580 A1 4/2004 Manna et al.
2004/0120904 A1 6/2004 Lye et al.
2004/0142041 A1 7/2004 MacDonald et al.
2004/0187524 A1 9/2004 Sen et al.
2004/0202728 A1 10/2004 Shanker et al.
2005/0000914 A1 1/2005 Dahlberg et al.
2005/0008560 A1 1/2005 Kataoka et al.
2005/0017599 A1 1/2005 Puskas
2005/0025797 A1 2/2005 Wang et al.
2005/0042129 A1 2/2005 Kazem
2005/0082234 A1 4/2005 Solenthaler
2005/0084438 A1 4/2005 Do et al.
2005/0084464 A1 4/2005 McGrath et al.
2005/0085144 A1 4/2005 MacDonald et al.
2005/0092931 A1 5/2005 Gadgil et al.
2005/0094486 A1 5/2005 Taniguchi
2005/0129161 A1 6/2005 Laberge
2005/0207431 A1 9/2005 Monai
2005/0220665 A1 10/2005 Ding
2005/0235740 A1 10/2005 Desie et al.
2005/0260106 A1 11/2005 Marhasin
2006/0000034 A1 1/2006 McGrath
2006/0008442 A1 1/2006 MacDonald et al.
2006/0120212 A1 6/2006 Taniguchi et al.
2006/0207431 A1 9/2006 Baca et al.
2007/0062801 A1 3/2007 Foret
2007/0114306 A1 5/2007 Kawakami et al.
2007/0119785 A1 5/2007 Englehardt et al.
2007/0131034 A1 6/2007 Ehlert et al.
2007/0170277 A1 7/2007 Ehlert et al.
2008/0061000 A1 3/2008 Janssen et al.
2008/0062811 A1 3/2008 Janssen et al.
2008/0063718 A1 3/2008 Janssen et al.
2008/0067418 A1 3/2008 Ross
2008/0069887 A1 3/2008 Baran et al.
2008/0117711 A1 5/2008 Omasa
2008/0155763 A1 7/2008 Janssen et al.
2008/0156737 A1 7/2008 Janssen et al.
2008/0159063 A1 7/2008 Janssen et al.
2008/0192568 A1 8/2008 Hielscher et al.
2008/0251375 A1 10/2008 Hielscher et al.
2009/0014377 A1 1/2009 Janssen et al.
2009/0147905 A1 6/2009 Janssen et al.
2009/0155091 A1 6/2009 Ehlert et al.
2009/0158936 A1 6/2009 Janssen et al.
2009/0162258 A1 6/2009 Janssen et al.
2009/0165654 A1 7/2009 Koenig et al.
2009/0166177 A1 7/2009 Wenzel et al.
2009/0168590 A1 7/2009 Koenig et al.
2009/0168591 A1 7/2009 Wenzel et al.
2009/0262597 A1 10/2009 Kieffer et al.
2010/0150859 A1 6/2010 Do et al.
2010/0206742 A1 8/2010 Janssen et al.
2010/0296975 A1 11/2010 Peshkovsky et al.
2013/0299737 A1 11/2013 Park et al.

FOREIGN PATENT DOCUMENTS

CN 1535249 A 10/2004
CN 1556120 12/2004
CN 1247628 C 3/2006
CN 101153138 4/2008
DE 2131878 A1 2/1973
DE 262553 A3 12/1988
DE 9017338 3/1991
DE 3922299 C1 4/1991
DE 4444525 6/1996
DE 19618217 A1 11/1997
DE 19854013 5/2000
DE 19913397 9/2000
DE 19938254 2/2001
DE 10015144 A1 10/2001
DE 29825063 6/2004
DE 202005009923 U1 4/2005
DE 102004040233 3/2006

(56) References Cited

FOREIGN PATENT DOCUMENTS

| | | | |
|---|---|---|---|
| DE | 102005025118 | | 1/2007 |
| DE | 102005034629 | | 1/2007 |
| EP | 0269941 | A1 | 6/1988 |
| EP | 0292470 | | 11/1988 |
| EP | 347891 | | 12/1989 |
| EP | 0457187 | A2 | 11/1991 |
| EP | 0459967 | | 12/1991 |
| EP | 625482 | | 11/1994 |
| EP | 648531 | | 4/1995 |
| EP | 0894612 | A2 | 2/1999 |
| EP | 1527812 | A1 | 4/2005 |
| EP | 1954388 | | 3/2007 |
| EP | 983968 | | 3/2008 |
| EP | 2173669 | A2 | 4/2010 |
| EP | 2176173 | A2 | 4/2010 |
| FR | 2793811 | | 11/2000 |
| FR | 2832703 | | 5/2003 |
| GB | 1404575 | | 9/1975 |
| JP | 56028221 | | 3/1981 |
| JP | 57119853 | | 7/1982 |
| JP | 5834051 | | 2/1983 |
| JP | 62039839 | U | 3/1987 |
| JP | 6372364 | | 4/1988 |
| JP | 63104664 | | 5/1988 |
| JP | 1108081 | | 4/1989 |
| JP | 2025602 | | 1/1990 |
| JP | 2281185 | A | 11/1990 |
| JP | 3053195 | A | 3/1991 |
| JP | 3086258 | | 4/1991 |
| JP | 3157129 | A | 7/1991 |
| JP | 6228824 | | 8/1994 |
| JP | 8304388 | | 11/1996 |
| JP | 9286943 | | 11/1997 |
| JP | 10060331 | | 3/1998 |
| JP | 11133661 | | 5/1999 |
| JP | 2000158364 | | 12/1999 |
| JP | 2001017970 | | 1/2001 |
| JP | 2001252588 | | 9/2001 |
| JP | 20020073778 | A | 9/2002 |
| JP | 2003103152 | A | 4/2003 |
| JP | 2004020176 | | 1/2004 |
| JP | 2004256783 | | 9/2004 |
| JP | 2005118688 | | 5/2005 |
| JP | 2007-144446 | | 6/2007 |
| JP | 2000024494 | A | 1/2010 |
| KR | 1020020073778 | A | 9/2002 |
| KR | 1020040069718 | | 8/2004 |
| KR | 1020050013858 | A | 2/2005 |
| KR | 1020050113356 | A | 12/2005 |
| SU | 203582 | A | 1/1967 |
| WO | 9400757 | | 1/1994 |
| WO | 9420833 | | 9/1994 |
| WO | 9429873 | A2 | 12/1994 |
| WO | 9600318 | | 1/1996 |
| WO | 9609112 | A1 | 3/1996 |
| WO | 9620017 | A1 | 7/1996 |
| WO | 9743026 | | 11/1997 |
| WO | 9817373 | | 4/1998 |
| WO | 9844058 | | 10/1998 |
| WO | 9933520 | | 7/1999 |
| WO | 0004978 | | 2/2000 |
| WO | 0041794 | | 7/2000 |
| WO | 0139200 | A2 | 5/2001 |
| WO | 0222252 | | 3/2002 |
| WO | 0250511 | | 6/2002 |
| WO | 02080668 | A2 | 10/2002 |
| WO | 03012800 | | 2/2003 |
| WO | 03102737 | | 12/2003 |
| WO | 2004026452 | | 4/2004 |
| WO | 2004064487 | | 8/2004 |
| WO | 2006037591 | | 4/2006 |
| WO | 2006043970 | A2 | 4/2006 |
| WO | 2006073645 | A1 | 7/2006 |
| WO | 2006074921 | A1 | 7/2006 |
| WO | 2006093804 | | 9/2006 |
| WO | 2007011520 | A2 | 1/2007 |
| WO | 2005011804 | | 5/2007 |
| WO | 2007060245 | A1 | 5/2007 |
| WO | 2007095871 | | 8/2007 |
| WO | 2008029311 | A1 | 3/2008 |
| WO | 2008029379 | | 3/2008 |
| WO | 2008047259 | A1 | 4/2008 |
| WO | 2008085806 | | 7/2008 |
| WO | 2009007920 | A2 | 1/2009 |
| WO | 2009083875 | A2 | 7/2009 |

OTHER PUBLICATIONS

Non-final Office action regarding U.S. Appl. No. 11/965,435, dated Mar. 11, 2010.

Non-final Office Action submitted in U.S. Appl. No. 11/530,183, dated Oct. 13, 2010.

Non-final Office Action submitted in U.S. Appl. No. 12/704,058, dated Dec. 9, 2010.

U.S. Appl. No. 11/966,472, filed Dec. 28, 2007.

Sivakumar et al., "Preparation of naosized TiO2 supported on activated alumina by a sonochemical method: observation of an increased photocatalytic decolourisation efficiency," Research on Chemical Intermediated, 30(7-8): 785-792 (2004).

Supplementary European Search Report issued in EP Application No. 08789242 mailed Dec. 17, 2010.

U.S. Appl. No. 11/966,447, filed Dec. 28, 2007.

Takehi Moriguchi, et al. "Metal-modified silica adsorbents for removal of humic substances in water." Journal of Colloid and Interface Science 283, 2005 300-310, See Abstract, pp. 301 and 304.

U.S. Appl. No. 11/617,497, filed Dec. 28, 2006.

U.S. Appl. No. 11/617,515, filed Dec. 28, 2006.

U.S. Appl. No. 11/950,943, filed Dec. 5, 2007.

U.S. Appl. No. 11/963,139, filed Dec. 21, 2007.

U.S. Appl. No. 11/965,435, filed Dec. 27, 2007.

U.S. Appl. No. 11/966,418, filed Dec. 28, 2007.

Compton R G et al., "Electrode Processes at the Surfaces of Sonotrodes," Electrochimica ACTA, vol. 41, No. 2, pp. 315-320 (Feb. 1, 1996).

Extended European Search Report received in EP Patent Application No. 08789246.9 mailed Nov. 30, 2011.

"Controlled Thermonuclear Fusion," viewed at http://library.thinkquest.org/17940/texts/fusion_controlled/fusion_controlled.html on Oct. 23, 2007.

"Thermonuclear Fusion Energy Source for Future Generations," viewed at http://www.crppwww.epfl.ch/crppfusion/ on Oct. 23, 2007.

Flannigan, "Measurement of Pressure and Density Inside a Single Sonoluminescing Bubble," Physical Review Letters (May 26, 2006), PRL 96.

International Search Report and Written Opinion regarding PCT/IB2007/052945, dated Feb. 1, 2008.

International Search Report and Written Opinion regarding PCT/IB2007/052947, dated Mar. 12, 2008.

International Search Report and Written Opinion regarding PCT/IB2007/052988, 4 pages, dated Feb. 14, 2008.

International Search Report and Written Opinion regarding PCT/IB2007/053621, dated Feb. 14, 2008.

International Search Report and Written Opinion regarding PCT/IB2007/053623, dated Feb. 14, 2008.

International Search Report and Written Opinion regarding PCT/IB2007/054892, dated May 15, 2008.

International Search Report and Written Opinion regarding PCT/IB2007/054898, dated May 15, 2008.

International Search Report regarding PCT/IB2007/053622, dated Feb. 14, 2008.

Kloeppel, James E., "Temperature inside collapsing bubble four times that of sun," News Bureau, University of Illinois at Urbana-Champaign.

Lahey, Taleyarkhan, and Nigmatulin, "Bubble Power," IEEE spectrum, May 2005, pp. 39-43.

Non-final office action regarding U.S. Appl. No. 11/530,311, dated Nov. 5, 2008.

(56) References Cited

OTHER PUBLICATIONS

Peplow, Mark, "Desktop fusion is back on the table," viewed at http://nature.com/news/2006/060109/full/060109-5.html on May 4, 2007.
Taleyarkhan, et al., "Additional Evidence of Nuclear Emissions During Acoustic Cavitation," Physcial Review E, (Mar. 2004). vol. 69.
Taleyarkhan, et al., "Evidence for Nuclear Emissions During Acoustic Cavitation," Science, (Mar. 8, 2002), vol. 295, pp. 1868-1873.
Tal-Figiel B., The Formation of Stable W/O, O/W, W/O/W Cosmetic Emulsions in an Ultrasonic Field, viewed at http://www.atypon-link.com/ICHEME/doi/abs/10.1205/cherd06199 on Oct. 19, 2007.
U.S. Appl. No. 11/777,140, filed Jul. 12, 2007.
U.S. Appl. No. 11/530,210, filed Sep. 8, 2006.
U.S. Appl. No. 11/530,311, filed Sep. 8, 2006.
U.S. Appl. No. 11/777,145, filed Jul. 12, 2007.
U.S. Appl. No. 11/777,151, filed Jul. 12, 2007.
U.S. Appl. No. 11/963,237, filed Dec. 21, 2007.
Brenner et al, Single-bubble sonoluminescence, Reviews of Modern Physics, vol. 74, Apr. 2002, pp. 425-484.
D.R.O. Morrison, "Cold Fusion Update No. 9", Jan. 1994, from Newsgroups sci.physics.fusion, http://www.groups.google.com.
J. Lister, Plasma Physics and Controlled Fusion 48, pp. 715-716 (2006).
J.D. Lawson, "Some Criteria for a Power Producing Thermonuclear Reactor", Proc. Phys. Soc. B70, pp. 6-10 (1957).
L.A. Artsimovich, "Controlled Thermonuclear Reactions", Gordon and Breach Science Publishers, New York, first English translation, 1964.
Non-final office action regarding U.S. Appl. No. 11/950,943, dated May 1, 2009.
U.S. Department of Energy, "Report of the Review of Low Energy Nuclear Reactions", Dec. 1, 2004 (USDOE).
Final Office Action Regarding U.S. Appl. No. 11/530,311, dated Jun. 23, 2009.
Non-final office action regarding U.S. Appl. No. 11/617,497, dated Jun. 26, 2009.
Barbaglia et al., "Search of Fusion Reactions During the Cavitation of a Single Bubble in Deuterated Liquids", Physica Scripta 72, pp. 75-78 (2005).
Blume, T. and Neis, U. "Improved wastewater disinfection by ultrasonic pre-treatment." Ultrasonics Sonochemistry, 2004, No. 11, pp. 333-336.
English translation of Nagel WO 2006/074921 A1, accessed on the EPO website.
European Office Action regarding European Application No. 07805228.9, dated Oct. 9, 2009.
Final Office Action Issued for U.S. Appl. No. 11/530,210 mailed Apr. 19, 2011.
Final Office Action issued for U.S. Appl. No. 11/530,210, mailed Jul. 1, 2011.
Final Office Action issued in related application U.S. Appl. No. 11/777,140 on Dec. 1, 2010.
Final Office Action issued in U.S. Appl. No. 11/530,183, dated Mar. 22, 2011.
Final Office Action issued in U.S. Appl. No. 11/966,418, mailed Jan. 12, 2011.
Final Office Action issued in U.S. Appl. No. 11/966,447, mailed Jan. 5, 2011.
Final Office Action issued in U.S. Appl. No. 11/966,458, dated Mar. 17, 2011.
Final Office Action issued in U.S. Appl. No. 12/335,231 dated Mar. 31, 2011.
Final Office Action Regarding U.S. Appl. No. 11/965,435, dated Mar. 11, 2010.
First Office Action for China Patent Application No. 200780033331.3, dated Nov. 14, 2011.
First Office Action for China Patent Application No. 200880121407.2, dated Aug. 24, 2011.
First Office Action for China Patent Application No. 20088016947.3, dated Jun. 24, 2011.
First Office Action for Russian Patent Application No. 2009112526, dated Apr. 28, 2011.
International Search Report and Written Opinion Issued for PCT/IB2008/052760, dated Feb. 17, 2009.
International Search Report and Written Opinion Issued for PCT/IB2008/052764, dated Apr. 2, 2009.
International Search Report and Written Opinion Issued for PCT/IB2008/052766, dated Mar. 31, 2009.
International Search Report and Written Opinion Issued for PCT/IB2008/055051, dated Feb. 20, 2009.
International Search Report and Written Opinion Issued for PCT/IB2008/055394, dated Sep. 28, 2009.
International Search Report and Written Opinion Issued for PCT/IB2008/055395, dated Sep. 14, 2009.
International Search Report and Written Opinion Issued for PCT/IB2008/055514, dated Aug. 25, 2009.
International Search Report and Written Opinion Issued for PCT/IB2008/055517, dated Aug. 18, 2009.
International Search Report and Written Opinion issued for PCT/IB2008/055518, dated Aug. 18, 2009.
International Search Report and Written Opinion Issued for PCT/IB2008/055520, dated Aug. 18, 2009.
International Search Report and Written Opinion regarding PCT/IB2008/055396, dated Jul. 29, 2009.
International Search Report and Written Opinion regarding PCT/IB2009/055090, dated Jul. 16, 2010.
International Search Report and Written Opinion regarding PCT/IB2009/055092, dated Jul. 16, 2010.
Kuo et al., "Nao-particles dispersion effect on Ni/Al2O3 Composite Coatings," Materials Chemistry and Physics, 86: 5-10 (2004).
Letter regarding the Office action issued for Mexican Patent Application No. MX/a/2009/002519, mailed on Oct. 12, 2010.
Moriguchi et al, "Metal-modified silica adsorbents for removal of humic substances in water", Journal of Colloidal and Interface Science 283 (2005) 300-310.
Non-Final Office Action issued for U.S. Appl. No. 11/963,139, mailed Jun. 15, 2011.
Non-Final Office Action issued for U.S. Appl. No. 12/335,176, mailed Jul. 13, 2011.
Non-Final Office Action issued for U.S. Appl. No. 12/335,231, mailed Jul. 13, 2011.
Non-final Office Action issued in related application U.S. Appl. No. 11/530,210 on Dec. 1, 2010.
Non-final Office Action issued in related application U.S. Appl. No. 11/530,210 on Jun. 28, 2010.
Non-final Office action issued in related application U.S. Appl. No. 11/777,140 on Aug. 9, 2010.
Non-final Office action issued in related application U.S. Appl. No. 11/966,418 on Aug. 2, 2010.
Non-final Office action issued in related application U.S. Appl. No. 11/966,447 on Aug. 2, 2010.
Non-final Office Action issued in U.S. Appl. No. 11/777,140, dated Feb. 23, 2011.
Non-final Office Action issued in U.S. Appl. No. 11/963,139, dated Feb. 18, 2011.
Non-final Office Action issued in U.S. Appl. No. 11/966,472, dated Mar. 31, 2011.
Non-final Office Action received in U.S. Appl. No. 11/966,458, mailed Sep. 28, 2010.
Non-final office action regarding U.S. Appl. No. 11/617,515, dated Mar. 27, 2009.
Non-final Office Action regarding U.S. Appl. No. 11/777,151, dated Dec. 8, 2010.
Non-final Office Action regarding U.S. Appl. No. 11/966,418, dated Jan. 12, 2011.
Non-final Office Action regarding U.S. Appl. No. 12/335,231, dated Oct. 15, 2009.
Non-final Office action regarding U.S. Appl. No. 11/530,183, dated Apr. 19, 2010.
Non-final Office Action received in U.S. Appl. No. 12/438,317, mailed Sep. 24, 2012.
Chinese Office Action for Patent Application No. 200880123174.X dated Mar. 27, 2013; 5 pages.

(56) References Cited

OTHER PUBLICATIONS

Extended European Search Report regarding European Application No. 13159386.5, dated May 3, 2013; 8 pages.
Extended European Search Report regarding European Application No. 08867345.4, dated Jul. 24, 2013; 8 pages.
European Communication received in EP Application No. 08868778.5, dated Oct. 22, 2014.
EP Office Action for Patent Application No. 08 789 246.9—2104 dated Sep. 4, 2012; 4 pages.
European Extended Search Report received in EP Application No. 08868778.5, dated Jul. 22, 2013.
Chinese First Office Action for Patent Application No. 200880123165.0 dated Oct. 10, 2012; 9 pages.
European Extended Search Report received in EP Application No. 08868912.0, dated Jan. 2, 2014.
European Search Report regarding European Application No. 08789248.5, dated May 2, 2013; 3 pages.
Non-Final Office Action for U.S. Appl. No. 11/530,210 dated Jul. 17, 2013; 14 pages.
Chinese First Office Action for Patent Application No. 200880123172.0 dated Oct. 10, 2012; 9 pages.
EP Office Action for Patent Application No. 08 789 248.5—2104 dated Sep. 4, 2012; 4 pages.
Extended European Search Report for EP Patent Application No. 08867871.9, mailed Sep. 27, 2012.
Mataar, et al., "Cellulose based organogel as an adsorbent for dissolved organic compounds," Industrial Crops and Products, vol. 49, pp. 33-42 (2013).
Zhang, et al. "Ultrasonic Regeneration of Granular Activated Carbon," Environmental Engineering Science, vol. 20, No. 1, pp. 57-64 (2003).

* cited by examiner

ULTRASONIC LIQUID TREATMENT AND DELIVERY SYSTEM AND PROCESS

CROSS-REFERENCE TO RELATED APPLICATIONS

This application is a U.S. National Stage patent application of International Application Serial Number PCT/IB2007/053622, filed on Sep. 7, 2007, which is a continuation-in-part application of U.S. patent application Ser. No. 11/780,860, filed on Jul. 20, 2007, now issued as U.S. Pat. No. 7,810,743, and is also a continuation-in-part application of U.S. patent application Ser. No. 11/530,311, filed on Sep. 8, 2006, now issued as U.S. Pat. No. 7,703,698, which is herein incorporated by reference in its entirety.

FIELD OF INVENTION

This invention relates generally to liquid treatment and delivery systems for treating and subsequently delivering an atomized spray of liquid, and more particularly to an ultrasonic liquid treatment and delivery system in which ultrasonic energy is applied to the liquid by the system prior to the liquid exiting the system.

BACKGROUND

Ultrasonic liquid delivery devices are used in various fields to energize liquid for the purpose of atomizing the liquid to provide a fine mist or spray of the liquid. For example, such devices are used as nebulizers and other drug delivery devices, molding equipment, humidifiers, fuel injection systems for engines, paint spray systems, ink delivery systems, mixing systems, homogenization systems, and the like. Such delivery devices typically comprise a housing that has a flow path through which the liquid flows in a pressurized state to at least one and sometimes a plurality of exhaust ports or orifices of the housing. The pressurized liquid is forced to exit the housing at the exhaust port(s). In some constructions, the device may include a valve member to control the flow of liquid from the device.

In some conventional ultrasonic liquid delivery devices, an ultrasonic excitation member is typically incorporated in the device, and more particularly forms the portion of the housing that defines the exhaust port(s). The excitation member is vibrated ultrasonically as liquid exits the exhaust port(s) to energize impart ultrasonic energy to the exiting liquid. The ultrasonic energy tends to atomize the liquid so that a spray of liquid droplets is delivered from the exhaust port(s). As an example, U.S. Pat. No. 5,330,100 (Malinowski) discloses a fuel injection system in which a nozzle (e.g., part of the housing) of the fuel injector is itself constructed to vibrate ultrasonically so that ultrasonic energy is imparted to the fuel as the fuel flows out through an exit orifice of the injector. In such a configuration, there is a risk that vibrating the nozzle itself will result in cavitation erosion (e.g., due to cavitation of the fuel within the exit orifice) of the nozzle at the exit orifice.

In other ultrasonic liquid delivery devices the ultrasonic excitation member may be disposed in the flow path through which liquid flows within the housing upstream of the exhaust port(s). Examples of such a device are disclosed in related U.S. Pat. No. 5,803,106 (Cohen et al.); U.S. Pat. No. 5,868,153 (Cohen et al.); U.S. Pat. No. 6,053,424 (Gipson et al.) and U.S. Pat. No. 6,380,264 (Jameson et al.), the disclosure of each of which is incorporated herein by reference. These references generally disclose a device for increasing the flow rate of a pressurized liquid through an orifice by applying ultrasonic energy to the pressurized liquid. In particular, pressurized liquid is delivered into the chamber of a housing having a die tip that includes an exit orifice (or exit orifices) through which the pressurized liquid exits the chamber.

An ultrasonic horn extends longitudinally in part within the chamber and in part outward of the chamber and has a diameter that decreases toward a tip disposed adjacent the exit orifice to amplify the ultrasonic vibration of the horn at its tip. A transducer is attached to the outer end of the horn to vibrate the horn ultrasonically. One potential disadvantage of such a device is that exposure of the various components to a high-pressure environment imparts substantial stress on the components. In particular, because part of the ultrasonic horn is immersed in the chamber and another part is not, there is a substantial pressure differential imparted to the different segments of the horn, resulting in additional stress on the horn. Moreover, such apparatus cannot readily accommodate an operating valve member, which is common in some ultrasonic liquid delivery devices to control the delivery of liquid from the device.

In still other liquid delivery devices, and in particular those that include an operating valve member to control liquid flow from the device, it is known to ultrasonically excite the valve member itself as liquid exits the device. For example, U.S. Pat. No. 6,543,700 (Jameson et al.), the disclosure of which is incorporated herein by reference, discloses a fuel injector in which a valve needle of the injector is formed at least in part of a magnetostrictive material responsive to magnetic fields changing at ultrasonic frequencies. When the valve needle is positioned to permit fuel to be exhausted from the valve body (i.e., the housing), a magnetic field changing at ultrasonic frequencies is applied to the magnetostrictive portion of the valve needle. Accordingly, the valve needle is ultrasonically excited to impart ultrasonic energy to the fuel as it exits the injector via the exit orifices.

As mentioned above, ultrasonic liquid delivery devices are used in various fields to energize various liquids. Some of these liquids are multiphase or multi-component liquids (e.g., aqueous solutions) that can undesirably separate. In one example, fuel oils can separate prior to being delivered to a combustion chamber, which can significantly decrease the efficiency of the chamber. Thus, it would be advantageous to mix the fuel oil just prior to it being delivered to the combustion chamber. Other applications besides the delivery of fuel oils suffer from this same shortcoming. Moreover, some applications require the ultrasonic liquid delivery devices span a predetermine distance to position the exit orifice in the proper location. As a result, it would be desirable to have an ultrasonic waveguide that can accommodate relatively long spans.

SUMMARY

In one embodiment, an ultrasonic liquid treatment and delivery system generally comprises an ultrasonic treatment device generally comprising a housing having an internal chamber and an inlet in fluid communication with the internal chamber of the housing whereby liquid enters the internal chamber and an outlet in fluid communication with the internal chamber of the housing through which liquid exits the ultrasonic treatment device. An ultrasonic waveguide is disposed at least in part within the internal chamber of the housing to ultrasonically energize liquid within the internal chamber prior to the liquid being exhausted from the housing through the outlet. The ultrasonic waveguide has an agitating member extending outward from the ultrasonic waveguide within the internal chamber of the housing intermediate the inlet and the outlet. The agitating member and the ultrasonic waveguide are constructed and arranged for dynamic motion of the agitating member relative to the ultrasonic waveguide upon ultrasonic vibration of the ultrasonic waveguide. An excitation device is operable to ultrasonically excite the ultrasonic waveguide and the agitating member.

The system also includes an ultrasonic delivery device in fluid communication with the ultrasonic treatment device to receive liquid from the ultrasonic treatment device following treatment of the liquid by said treatment device. The ultrasonic delivery device generally comprises a housing having an internal chamber, an inlet for receiving liquid from the treatment device into the internal chamber of the delivery device housing and at least one exhaust port in fluid communication with the internal chamber of the delivery device housing whereby liquid within said internal chamber exits the delivery device housing at said at least one exhaust port. An ultrasonic waveguide is separate from the delivery device housing and disposed at least in part within the internal chamber of the delivery device housing to ultrasonically energize liquid within the internal chamber prior to the liquid being exhausted from the housing through the at least one exhaust port. An excitation device is operable to ultrasonically excite the ultrasonic waveguide of the delivery device.

In another embodiment, an ultrasonic liquid treatment and delivery system generally comprises an ultrasonic treatment device that includes a housing having an inlet for receiving liquid into the housing, an outlet through which liquid exits the treatment device housing, and an internal flow path in fluid communication with the inlet and the outlet to direct the flow of liquid within the housing from said inlet to said outlet. An ultrasonic waveguide is separate from the housing and is disposed at least in part within the flow path to ultrasonically energize liquid within the flow path. The ultrasonic waveguide has an agitating member extending outward from the ultrasonic waveguide within the flow path, with the agitating member and the ultrasonic waveguide being constructed and arranged for dynamic motion of the agitating member relative to the ultrasonic waveguide upon ultrasonic vibration of the ultrasonic waveguide. An excitation device is operable to ultrasonically excite the ultrasonic waveguide and the agitating member.

The system also includes an ultrasonic delivery device in fluid communication with the ultrasonic treatment device to receive liquid from the ultrasonic treatment device following treatment of the liquid by the treatment device. The ultrasonic delivery device generally comprises a housing having an internal chamber, an inlet for receiving liquid from the treatment device into the internal chamber of the delivery device housing and at least one exhaust port in fluid communication with the internal chamber of the delivery device housing whereby liquid within the internal chamber exits the delivery device housing at the at least one exhaust port. An ultrasonic waveguide is separate from the delivery device housing and is disposed at least in part within the internal chamber of the delivery device housing to ultrasonically energize liquid within the internal chamber prior to the liquid being exhausted from the housing through the at least one exhaust port. An excitation device is operable to ultrasonically excite the ultrasonic waveguide of the delivery device.

In one embodiment, a process for ultrasonically treating a liquid and delivering the liquid as a spray of liquid droplets generally comprises directing the liquid to flow along a flow path over a first ultrasonic waveguide, with the first ultrasonic waveguide having at least one agitating member extending outward therefrom and into the flow path for contact with the liquid flowing along the flow path. The first ultrasonic waveguide and the at least one agitating member are excited to agitate the liquid as the liquid flows over the ultrasonic waveguide and agitating member. The liquid is further directed to flow along the flow path over a second waveguide, with the second waveguide having a terminal end adjacent an exit of the flow path such that liquid flowing along the flow path flows over the terminal end of the second waveguide prior to the liquid exiting the flow path. The second ultrasonic waveguide is ultrasonically excited at least at its terminal end to ultrasonically energize the liquid just prior to the liquid exiting the flow path such that the liquid exits the flow path as a spray of liquid droplets.

BRIEF DESCRIPTION OF THE DRAWINGS

Corresponding reference characters indicate corresponding parts throughout the drawings.

DETAILED DESCRIPTION

Figure 1:
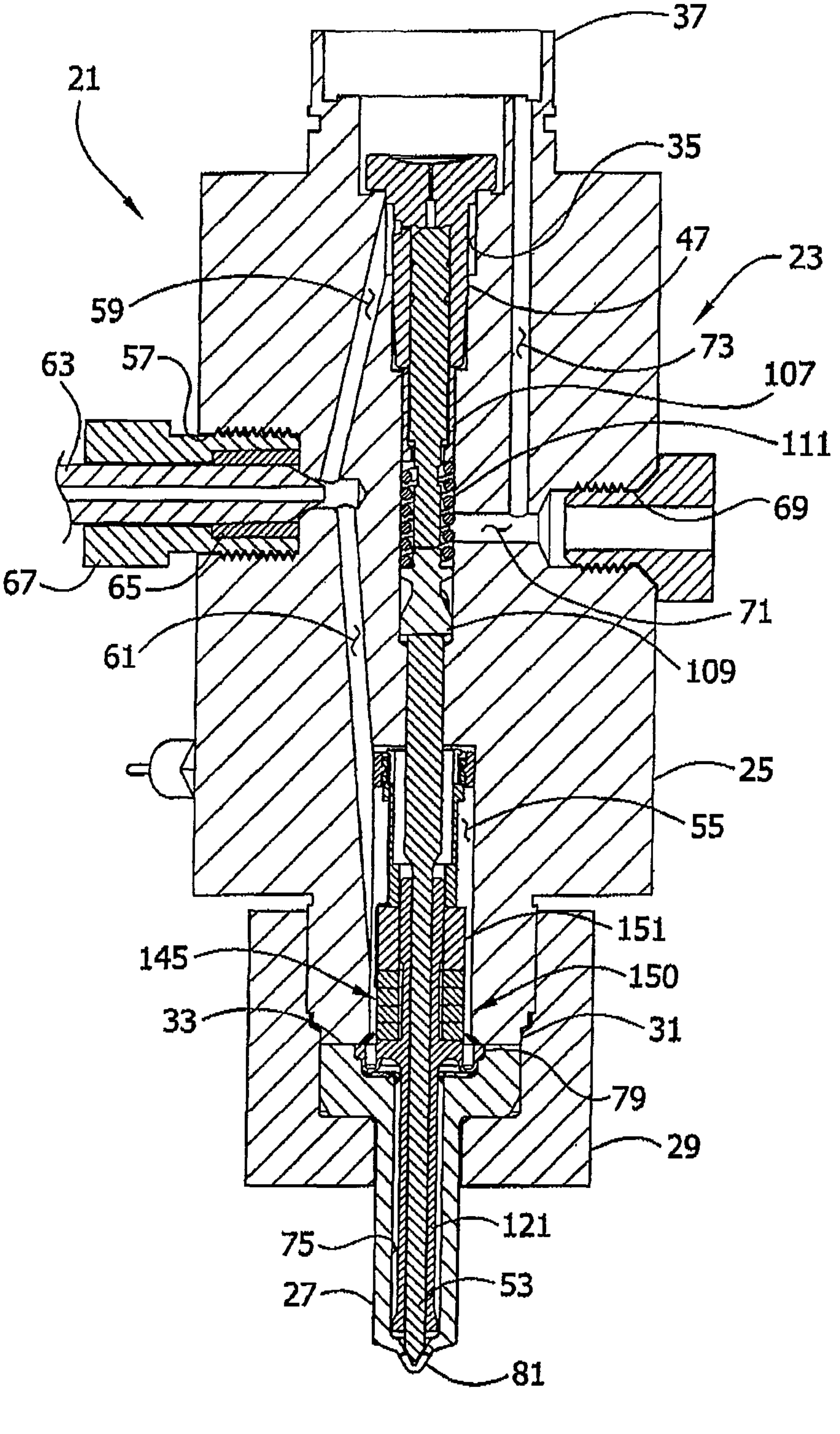
FIG. 1 is a longitudinal cross-section of one embodiment of an ultrasonic liquid delivery device of the present invention illustrated in the form of a fuel injector for delivering fuel to an internal combustion engine.

With reference now to the drawings and in particular to FIG. 1, an ultrasonic liquid delivery device according to one embodiment of the present invention is illustrated in the form of an ultrasonic fuel injector for use with an internal combustion engine (not shown) and is generally designated 21. It is understood, however, that the concepts disclosed herein in relation to the fuel injector 21 are applicable to the other ultrasonic liquid delivery devices including, without limitation, nebulizers and other drug delivery devices, molding equipment, humidifiers, paint spray systems, ink delivery systems, mixing systems, homogenization systems, and the like.

The term liquid, as used herein, refers to an amorphous (noncrystalline) form of matter intermediate between gases and solids, in which the molecules are much more highly concentrated than in gases, but much less concentrated than in solids. The liquid may comprise a single component or may be comprised of multiple components. For example, characteristic of liquids is their ability to flow as a result of an applied force. Liquids that flow immediately upon application of force and for which the rate of flow is directly proportional to the force applied are generally referred to as Newtonian liquids. Other suitable liquids have abnormal flow response when force is applied and exhibit non-Newtonian flow properties.

As examples, the ultrasonic liquid delivery device of the present invention may be used to deliver liquids such as, without limitation, molten bitumens, viscous paints, hot melt adhesives, thermoplastic materials that soften to a flowable form when exposed to heat and return to a relatively set or hardened condition upon cooling (e.g., crude rubber, wax, polyolefins and the like), syrups, heavy oils, inks, fuels, liquid medication, emulsions, slurries, suspensions and combinations thereof.

The fuel injector 21 illustrated in FIG. 1 may be used with land, air and marine vehicles, electrical power generators and other devices that employ a fuel operated engine. In particular, the fuel injector 21 is suitable for use with engines that use diesel fuel. However, it is understood that the fuel injector is useful with engines that use other types of fuel. Accordingly, the term fuel as used herein is intended to mean any combustible fuel used in the operation of an engine and is not limited to diesel fuel.

The fuel injector 21 comprises a housing, indicated generally at 23, for receiving pressurized fuel from a source (not shown) of fuel and delivering an atomized spray of fuel droplets to the engine, such as to a combustion chamber of the engine. In the illustrated embodiment, the housing 23 comprises an elongate main body 25, a nozzle 27 (sometimes also referred to as a valve body) and a retaining member 29 (e.g., a nut) holding the main body, nozzle and nut in assembly with each other. In particular, a lower end 31 of the main body 25 seats against an upper end 33 of the nozzle 27. The retaining member 29 suitably fastens (e.g., threadably fastens) to the outer surface of the main body 25 to urge the mating ends 31, 33 of the main body and nozzle 27 together.

The terms "upper" and "lower" are used herein in accordance with the vertical orientation of the fuel injector 21 illustrated in the various drawings and are not intended to describe a necessary orientation of the fuel injector in use. That is, it is understood that the fuel injector 21 may be oriented other than in the vertical orientation illustrated in the drawings and remain within the scope of this invention. The terms axial and longitudinal refer directionally herein to the lengthwise direction of the fuel injector (e.g., the vertical direction in the illustrated embodiments). The terms transverse, lateral and radial refer herein to a direction normal to the axial (e.g., longitudinal) direction. The terms inner and outer are also used in reference to a direction transverse to the axial direction of the fuel injector, with the term inner referring to a direction toward the interior of the fuel injector and the term outer referring to a direction toward the exterior of the injector.

The main body 25 has an axial bore 35 extending longitudinally along its length. The transverse, or cross-sectional dimension of the bore 35 (e.g., the diameter of the circular bore illustrated in FIG. 1) varies along discrete longitudinal segments of the bore for purposes which will become apparent. In particular, with reference to FIG. 3, at an upper end 37 of the main body 25 the cross-sectional dimension of the bore 35 is stepped to form a seat 39 for seating a conventional solenoid valve (not shown) on the main body with a portion of the solenoid valve extending down within the central bore of the main body. The fuel injector 21 and solenoid valve are held together in assembly by a suitable connector (not shown). Construction and operation of suitable solenoid valves are known to those skilled in the art and are therefore not described further herein except to the extent necessary. Examples of suitable solenoid valves are disclosed in U.S. Pat. No. 6,688,579 entitled "Solenoid Valve for Controlling a Fuel Injector of an Internal Combustion Engine," U.S. Pat. No. 6,827,332 entitled "Solenoid Valve," and U.S. Pat. No. 6,874,706 entitled "Solenoid Valve Comprising a Plug-In/Rotative Connection." Other suitable solenoid valves may also be used.

Figure 4:
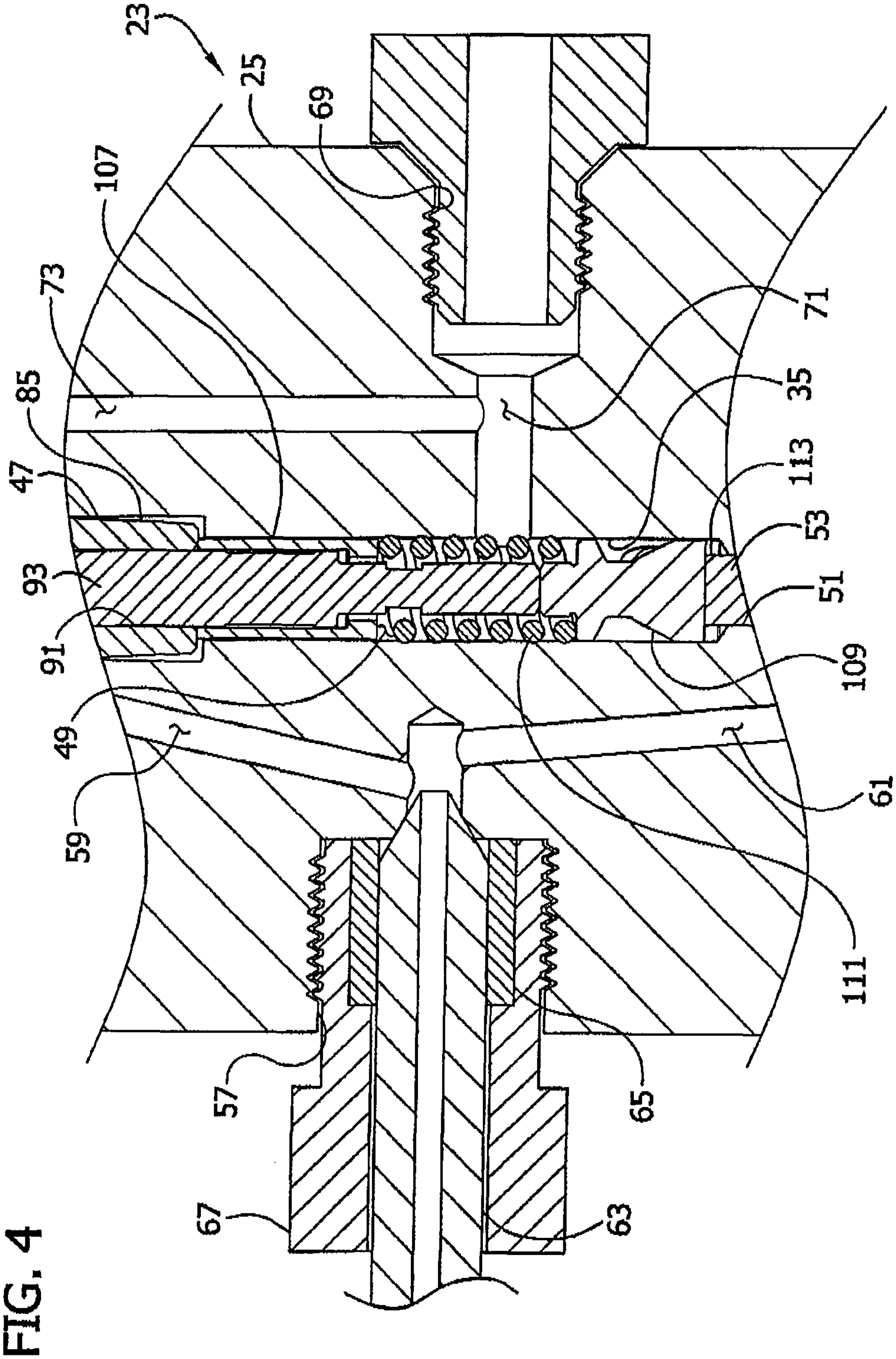
FIG. 4 is an expanded view of a second portion of the cross-section of the FIG. 1.

The cross-sectional dimension of the central bore 35 is stepped further inward as it extends below the solenoid valve seat to define a shoulder 45 which seats a pin holder 47 that extends longitudinally (and coaxially in the illustrated embodiment) within the central bore. As illustrated in FIG. 4, the bore 35 of the main body 25 further narrows in cross-section as it extends longitudinally below the segment of the bore in which the pin holder 47 extends, and defines at least in part a low pressure chamber 49 of the injector 21.

Figure 8:
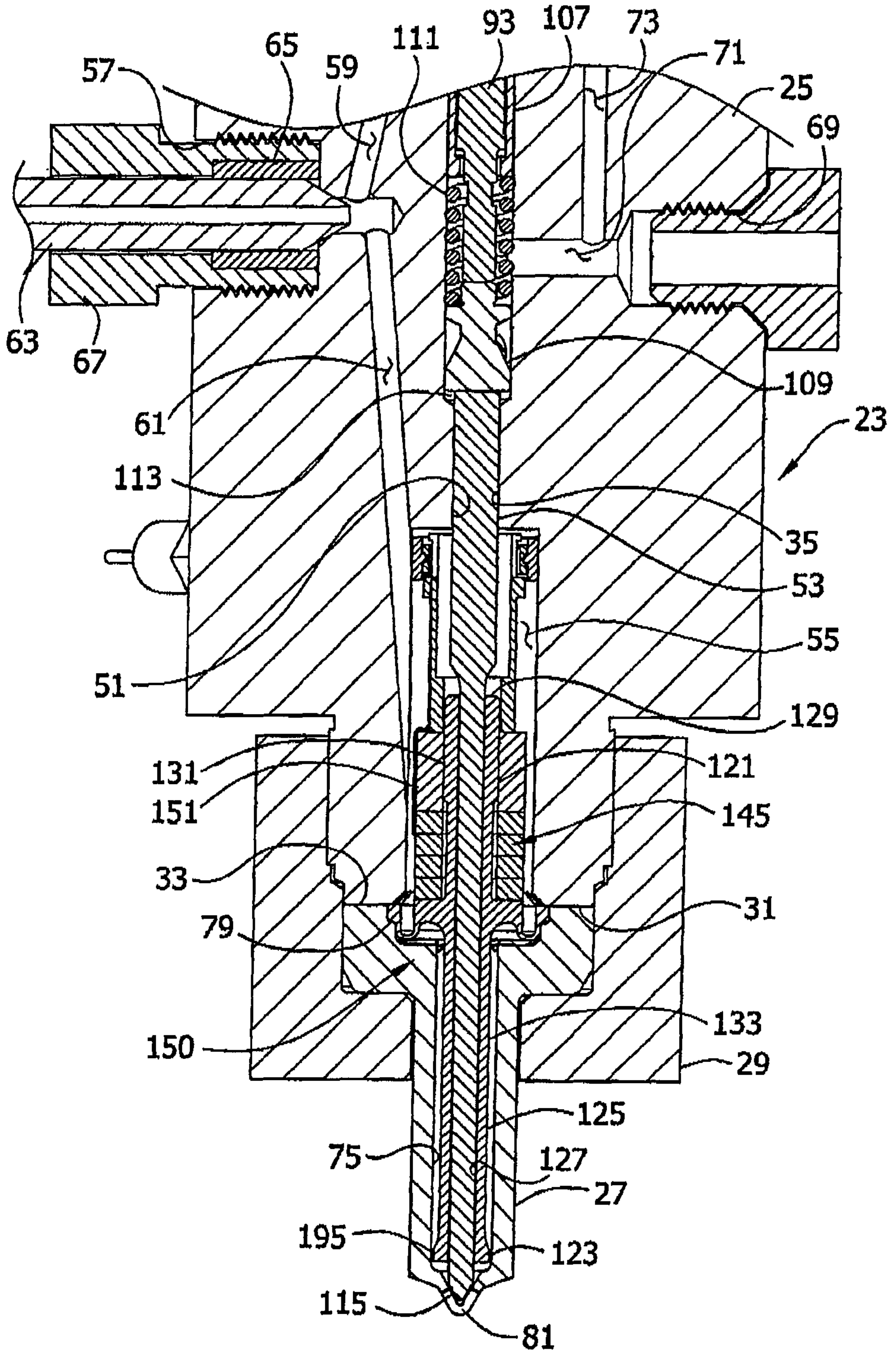
FIG. 8 is a fragmented and enlarged view of the cross-section of FIG. 1.

Longitudinally below the low pressure chamber 49, the central bore 35 of the main body 25 narrows even further to define a guide channel (and high pressure sealing) segment 51 (FIGS. 4 and 5) of the bore for at least in part properly locating a valve needle 53 (broadly, a valve member) of the injector 21 within the bore as described later herein. With reference to FIG. 8, the cross-sectional dimension of the bore 35 then increases as the bore extends longitudinally below the guide channel segment 51 to the open lower end 31 of the main body 25 to in part (e.g. together with the nozzle 27 as will be described) define a high pressure chamber 55 (broadly, an internal fuel chamber and even more broadly an internal liquid chamber) of the injector housing 23.

A fuel inlet 57 (FIGS. 1 and 4) is formed in the side of the main body 25 intermediate the upper and lower ends 37, 31 thereof and communicates with diverging upper and lower distribution channels 59, 61 extending within the main body. In particular, the upper distribution channel 59 extends from the fuel inlet 57 upward within the main body 25 and opens into the bore 35 generally adjacent the pin holder 47 secured within the bore, and more particularly just below the shoulder 45 on which the pin holder is seated. The lower distribution channel 61 extends from the fuel inlet 57 down within the main body 25 and opens into the central bore 35 generally at the high pressure chamber 55. A delivery tube 63 extends inward through the main body 25 at the fuel inlet 57 and is held in assembly with the main body by a suitable sleeve 65 and threaded fitting 67. It is understood that the fuel inlet 57 may be located other than as illustrated in FIGS. 1 and 4 without departing from the scope of the invention. It is also understood that fuel may delivered solely to the high pressure chamber 55 of the housing 23 and remain within the scope of this invention.

The main body 25 also has an outlet 69 (FIGS. 1 and 4) formed in its side through which low pressure fuel is exhausted from the injector 21 for delivery to a suitable fuel return system (not shown). A first return channel 71 is formed in the main body 25 and provides fluid communication between the outlet 69 and the low pressure chamber 49 of the central bore 35 of the main body. A second return channel 73 is formed in the main body 25 to provide fluid communication between the outlet 69 and the open upper end 37 of the main body. It is understood, however, that one or both of the return channels 71, 73 may be omitted from the fuel injector 21 without departing from the scope of this invention.

Figure 6:
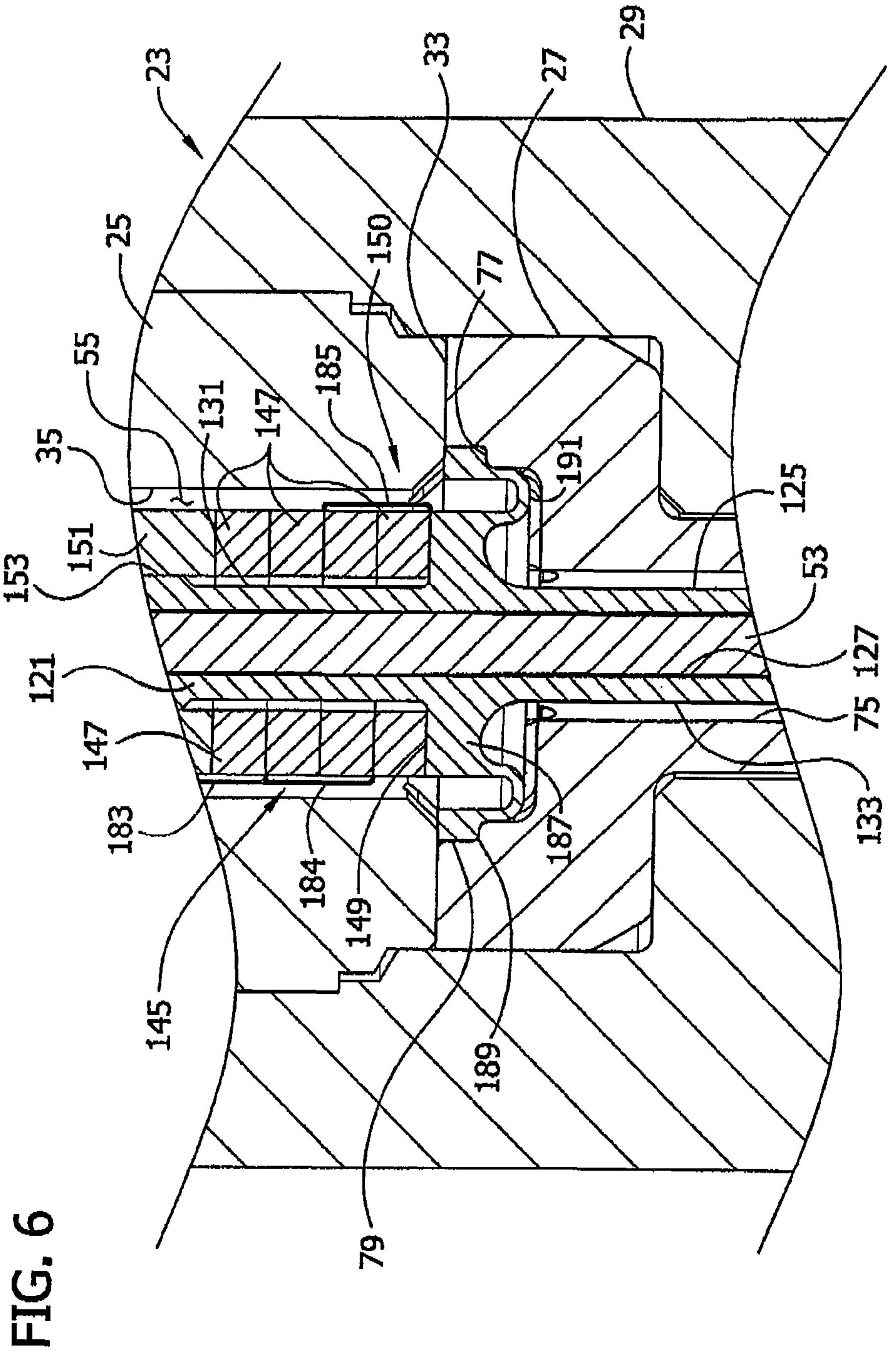
FIG. 6 is an expanded view of a fourth portion of the cross-section of FIG. 1.
Figure 7:
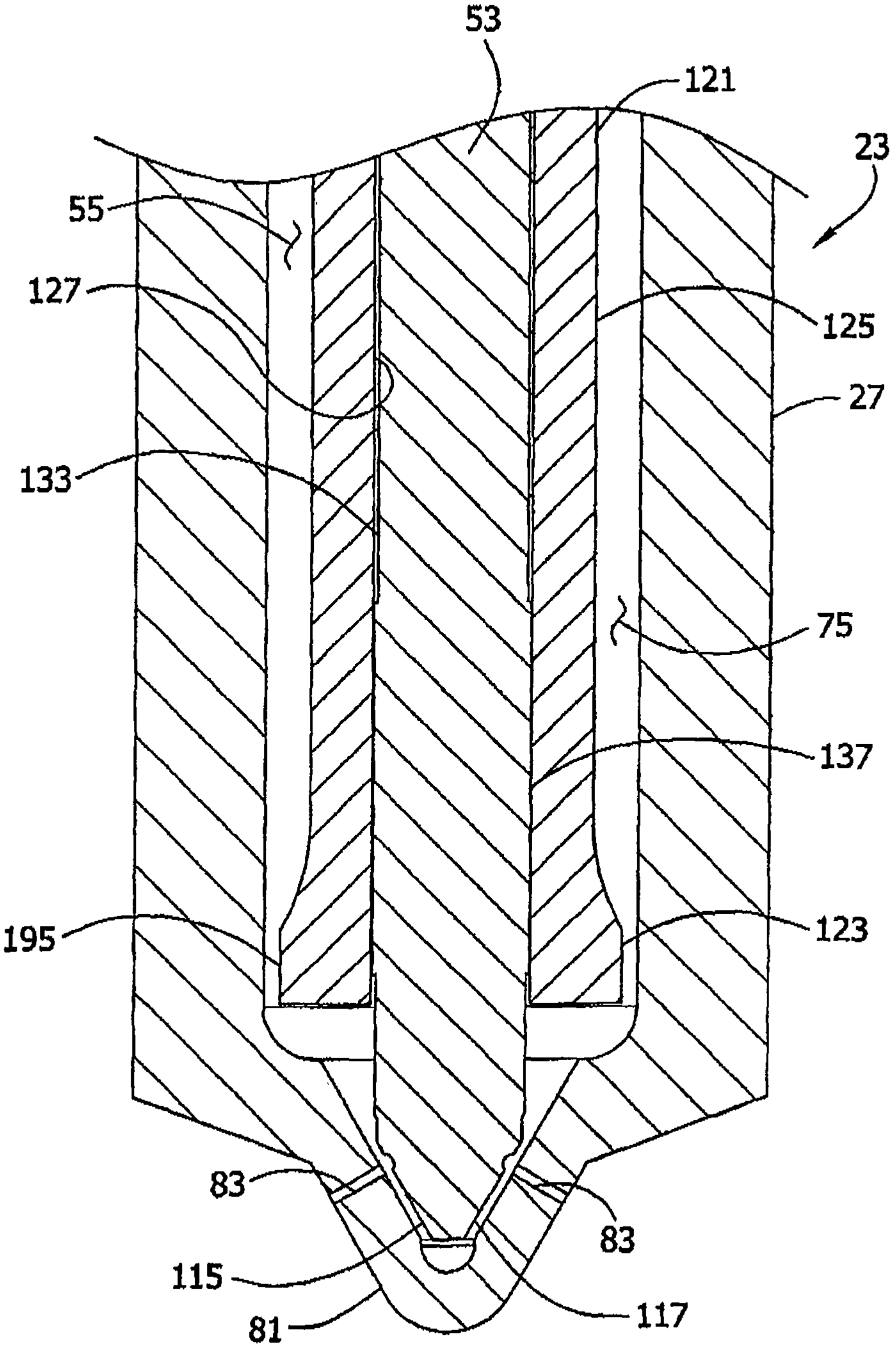
FIG. 7 is an expanded view of a fifth portion of the cross-section of FIG. 1.

With particular reference now to FIGS. 6-8, the illustrated nozzle 27 is generally elongate and is aligned coaxially with the main body 25 of the fuel injector housing 23. In particular, the nozzle 27 has an axial bore 75 aligned coaxially with the axial bore 35 of the main body 25, particularly at the lower end 31 of the main body, so that the main body and nozzle together define the high pressure chamber 55 of the fuel injector housing 23. The cross-sectional dimension of the nozzle bore 75 is stepped outward at the upper end 33 of the nozzle 27 to define a shoulder 77 for seating a mounting member 79 in the fuel injector housing 23. The lower end (also referred to as a tip 81) of the nozzle 27 is generally conical.

Intermediate its tip 81 and upper end 33 the cross-sectional dimension (e.g. the diameter in the illustrated embodiment) of the nozzle bore 75 is generally uniform along the length of the nozzle as illustrated in FIG. 8. One or more exhaust ports 83 (two are visible in the cross-section of FIG. 7 while additional ports are visible in the cross-section of FIG. 10) are formed in the nozzle 27, such as at the tip 81 of the nozzle in the illustrated embodiment, through which high pressure fuel is exhausted from the housing 23 for delivery to the engine. As an example, in one suitable embodiment the nozzle 27 may have eight exhaust ports 83, with each exhaust port having a diameter of about 0.006 inches (0.15 mm). However, it is understood that the number of exhaust ports and the diameter thereof may vary without departing from the scope of this invention. The lower distribution channel 61 and the high pressure chamber 55 together broadly define herein a flow path within the housing 23 along which high pressure fuel flows from the fuel inlet 57 to the exhaust ports 83 of the nozzle 27.

Figure 3:
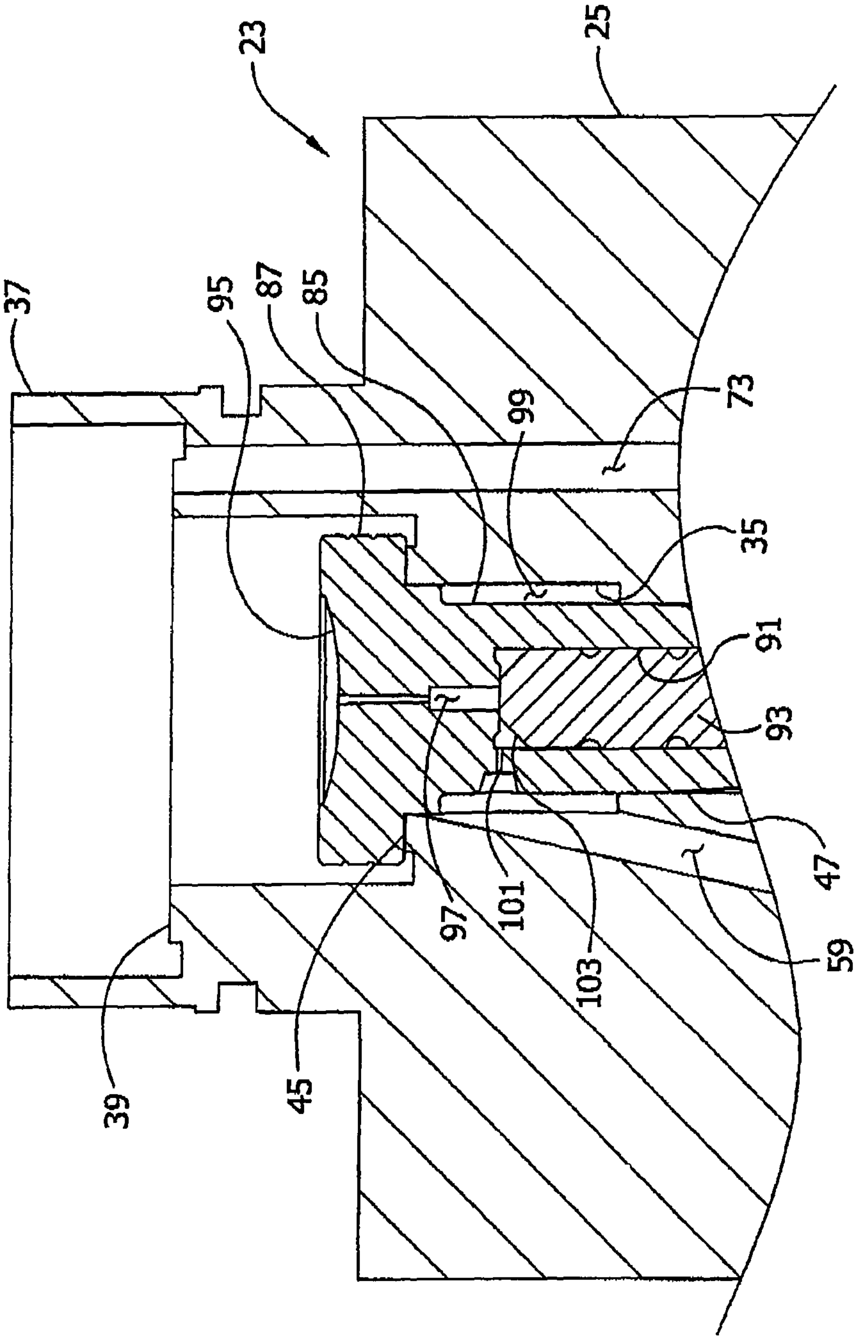
FIG. 3 is an expanded view of a first portion of the cross-section of FIG. 1.

Referring now to FIGS. 1 and 3, the pin holder 47 comprises an elongate, tubular body 85 and a head 87 formed integrally with the upper end of the tubular body and sized in transverse cross-section greater than the tubular body for locating the pin holder on the shoulder 45 of the main body 25 within the central bore 35 thereof. In the illustrated embodiment the pin holder 47 is aligned coaxially with the axial bore 35 of the main body 25, with the tubular body 85 of the pin holder being sized for generally sealing engagement with main body within the axial bore of the main body. The tubular body 85 of the pin holder 47 defines a longitudinally extending internal channel 91 of the pin holder for slidably receiving an elongate pin 93 into the pin holder.

The head 87 of the pin holder 47 has a generally concave, or dish-shaped recess 95 formed centrally in its upper surface, and a bore 97 that extends longitudinally from the center of this recess to the internal channel 91 of the pin holder. As illustrated in FIG. 3, an annular gap 99 is formed between the sidewall of the pin holder 47 and the inner surface of the main body 25 at the upper portion of the bore 35 of the main body. A feed channel 101 extends transversely through the sidewall of the tubular body 85 of the pin holder 47 to the internal channel 91 generally at the upper end of the channel, with the feed channel 101 being open at its transverse outer end to the annular gap 99. The feed channel 101 is in fluid communication with the upper distribution channel 59 in the main body

25 via the annular gap 99 for receiving high pressure fuel into the feed channel, the internal channel of the tubular body 85 above the pin 93, and the bore 97 extending longitudinally within the head 87 of the pin holder 47.

The pin 93 is elongate and suitably extends coaxially within the pin holder channel 91 and axial bore 35 of the main body 25. An upper segment of the pin 93 is slidably received within the internal channel 91 of the pin holder 47 in closely spaced relationship therewith while the remainder of the pin extends longitudinally outward from the pin holder down into the low pressure chamber 49 of the bore 35 of the main body 25. As illustrated in FIG. 3, an upper end 103 of the pin 93 (e.g., at the top of the internal channel 101 of the pin holder 47) is tapered to permit high pressure fuel to be received within the internal channel of the pin holder above the upper end of the pin.

Also disposed within the low pressure chamber 49 of the main body bore 35 are a tubular sleeve 107 (FIG. 4) that surrounds the pin 93 just below the pin holder 47 (e.g., abutting up against the bottom of the pin holder) and defines a spring seat, a hammer 109 abutting against the lower end of the pin in coaxial relationship with the pin and having an upper end that defines an opposing spring seat, and a coil spring 111 retained between the hammer and the spring sleeve with the pin passing longitudinally through the spring.

Figure 2:
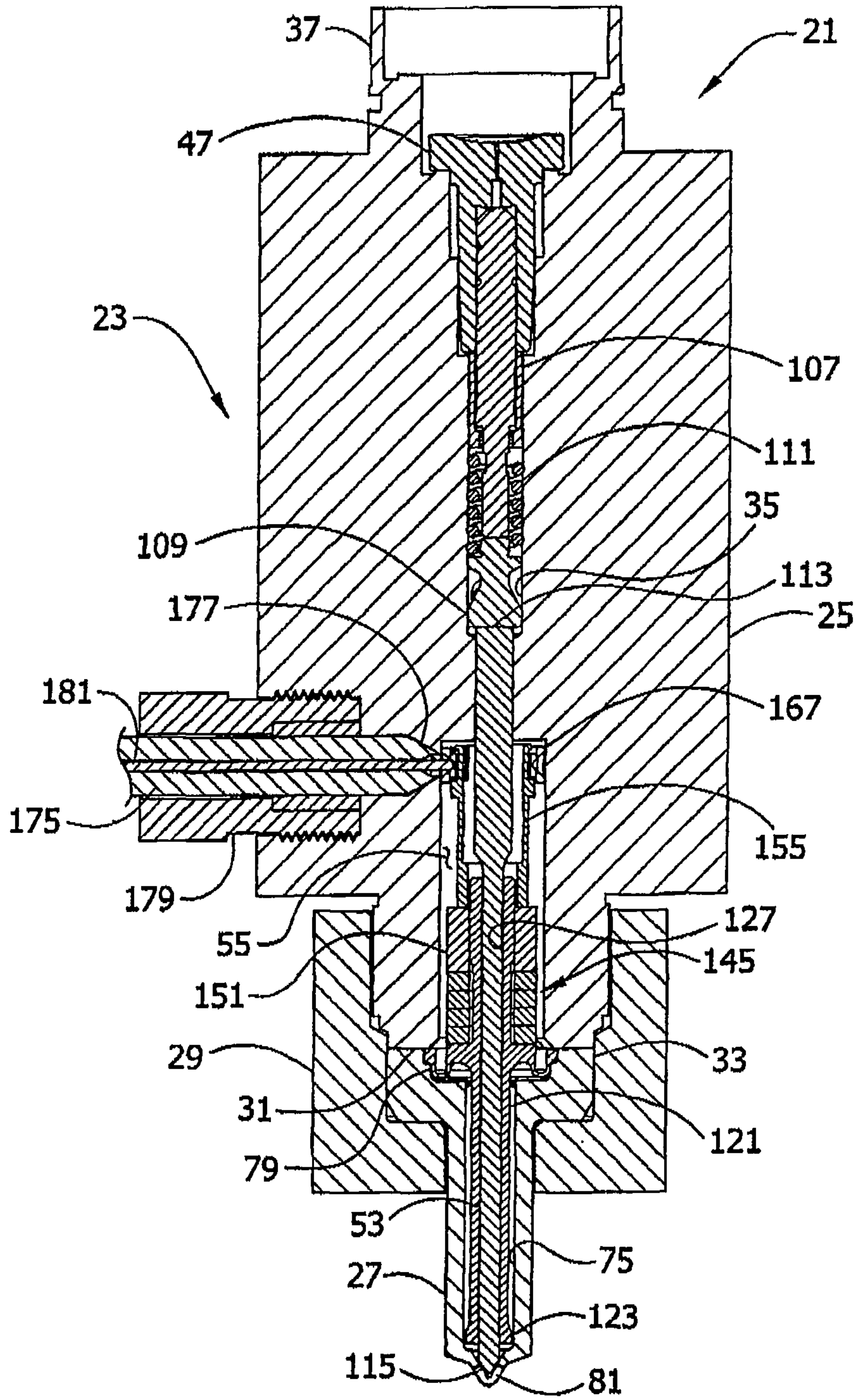
FIG. 2 is a longitudinal cross-section of the fuel injector of FIG. 1 taken at an angular position different from that at which the cross-section of FIG. 1 is taken.

The valve needle 53 (broadly, the valve member) is elongate and extends coaxially within the bore 35 of the main body 25 from an upper end 113 (FIG. 2) of the valve needle in abutment with the bottom of the hammer 109, down through the guide channel segment 51 (FIG. 8) of the main body bore, and further down through the high pressure chamber 55 to a terminal end 115 of the valve needle disposed in close proximity to the tip 81 of the nozzle 27 within the high pressure chamber. As illustrated best in FIGS. 4 and 8, the valve needle 53 is sized in transverse cross-section for closely spaced relationship with the main body 25 in the guide channel segment 51 of the axial bore 35 to maintain proper alignment of the valve needle relative to the nozzle 27.

Referring particularly to FIG. 7, the terminal end 115 of the illustrated valve needle 53 is generally conical in accordance with the conical shape of the tip 81 of the nozzle 27 and defines a closure surface 117 adapted for generally sealing against the inner surface of the nozzle tip in a closed position (not shown) of the valve needle. In particular, in the closed position of the valve needle 53 the closure surface 117 of the valve needle seals against the inner surface of the nozzle tip 81 over the exhaust ports 83 to seal the nozzle (and more broadly the fuel injector housing 23) against fuel being exhausted from the nozzle via the exhaust ports. In an open position of the valve needle (illustrated in FIG. 7), the closure surface 117 of the valve needle 53 is spaced from the inner surface of the nozzle tip 81 to permit fuel in the high pressure chamber 55 to flow between the valve needle 53 and nozzle tip 81 to the exhaust ports 83 for exhaustion from the fuel injector 21.

In general, the spacing between the closure surface 117 of the valve needle terminal end 115 and the opposed surface of nozzle tip 81 in the open position of the valve needle is suitably in the range of about 0.002 inches (0.051 mm) to about 0.025 inches (0.64 mm). However, it is understood that the spacing may be greater or less than the range specified above without departing from the scope of this invention.

It is contemplated that the nozzle 27, and more particularly the tip 81, may be alternatively configured such that the exhaust ports 83 are disposed other than on the nozzle inner surface that seats the closure surface 117 of the valve needle 53 in the closed position of the valve needle. For example, the exhaust ports 83 may be disposed downstream (in the direction in which fuel flows toward the exhaust ports) of the nozzle surface that seats the closure surface 117 of the valve needle 53 and remain within the scope of this invention. One suitable example of such a valve needle, nozzle tip and exhaust port arrangement is described in U.S. Pat. No. 6,543,700, the disclosure of which is incorporated herein by reference to the extent it is consistent herewith.

It will be understood that the pin 93, the hammer 109 and the valve needle 53 are thus conjointly moveable longitudinally on a common axis within the fuel injector housing 23 between the closed position and the open position of the valve needle. The spring 111 disposed between the sleeve 107 and the hammer 109 suitably biases the hammer, and thus the valve needle 53, toward the closed position of the valve needle. It is understood that other suitable valve configurations are possible for controlling the flow of fuel from the injector for delivery to the engine without departing from the scope of this invention. For example, the nozzle 27 (broadly, the housing 23) may have an opening through which the valve needle 53 extends outward of the nozzle and through which fuel exits the nozzle for delivery to the engine. In such an embodiment the terminal end 115 of the valve needle 53 would seal against the nozzle 27 exterior thereof in the closed position of the valve needle. It is also understood that operation of the valve needle 53 may be controlled other than by a solenoid valve and remain within the scope of this invention. It is further understood that the valve needle 53 or other valve arrangement may be omitted altogether from the fuel injector 21 without departing from the scope of this invention.

Figure 9:
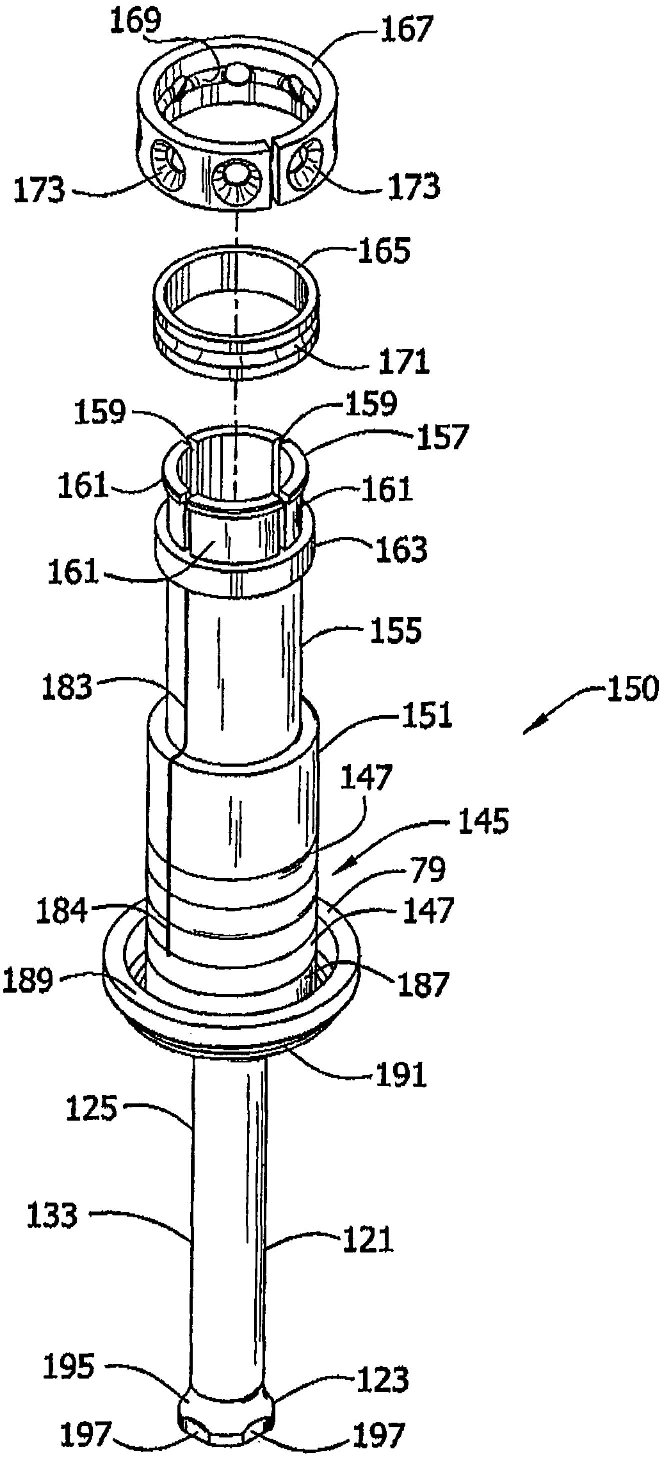
FIG. 9 is a perspective view of a waveguide assembly and other internal components of the fuel injector of FIG. 1.

With particular reference now to FIGS. 8 and 9, an ultrasonic waveguide 121 is formed separate from the valve needle 53 and the fuel injector housing 23 and extends longitudinally within the high pressure chamber 55 of the housing to a terminal end 123 of the waveguide disposed just above the tip 81 of the nozzle 27 to ultrasonically energize fuel in the fuel chamber just prior to the fuel exiting the injector 21 via the exhaust ports 83 formed in the nozzle. The illustrated waveguide 121 is suitably elongate and tubular, having a sidewall 125 defining an internal passage 127 that extends along its length between longitudinally opposite upper and lower ends (the upper end being indicated at 129) of the waveguide. The lower end of the waveguide 121 defines the terminal end 123 of the waveguide. The illustrated waveguide 121 has a generally annular (i.e., circular) cross-section. However, it is understood that the waveguide 121 may be shaped in cross-section other than annular without departing from the scope of this invention. It is also contemplated that the waveguide 121 may be tubular along less than its entire length, and may even be generally solid along its length. In other embodiments, it is contemplated that the valve needle may be generally tubular and the waveguide disposed at least in part within the interior of the valve needle.

In general, the waveguide may be constructed of a metal having suitable acoustical and mechanical properties. Examples of suitable metals for construction of the waveguide include, without limitation, aluminum, monel, titanium, and some alloy steels. It is also contemplated that all or part of the waveguide may be coated with another metal. The ultrasonic waveguide 121 is secured within the fuel injector housing 23, and more suitably in the high pressure chamber 55 as in the illustrated embodiment, by the mounting member 79. The mounting member 79, located longitudinally between the ends 123, 129 of the waveguide 121, generally defines an upper segment 131 of the waveguide that extends longitudinally up (in the illustrated embodiment) from the mounting member 79 to the upper end 129 of the waveguide and a lower segment 133 that extends longitudinally down from the mounting member to the terminal end 123 of the waveguide.

While in the illustrated embodiment the waveguide 121 (i.e., both the upper and lower segments thereof) is disposed entirely within the high pressure chamber 55 of the housing, it is contemplated that only a portion of the waveguide may be disposed within the high pressure chamber without departing from the scope of this invention. For example, only the lower segment 133 of the waveguide 121, including the terminal end 123 thereof, may be disposed within the high pressure chamber 55 while the upper segment 131 of the waveguide is disposed exterior of the high pressure chamber, and may or may not be subjected to high pressure fuel within the injector housing 23.

The inner cross-sectional dimension (e.g., inner diameter in the illustrated embodiment) of the waveguide 121 (e.g., the cross-sectional dimension of the interior passage 127 thereof) is generally uniform along the length of the waveguide and is suitably sized to accommodate the valve needle 53, which extends coaxially within the interior passage of the waveguide along the full length of the waveguide (and above the waveguide into abutment with the hammer 109 in the illustrated embodiment). It is understood, however, that the valve needle 53 may extend only along a portion of the interior passage 127 of the waveguide 121 without departing from the scope of this invention. It is also understood that the inner cross-sectional dimension of the waveguide 121 may be other than uniform along the length of the waveguide. In the illustrated embodiment, the terminal end 115 of the valve needle 53, and more suitably the closure surface 117 of the valve needle, is disposed longitudinally outward of the terminal end 123 of the waveguide 121 in both the open and closed positions of the valve needle. It is understood, however, that the closure surface 117 of the terminal end 115 of the valve needle 53 need only extend outward of the terminal end 123 of the waveguide 121 in the closed position of the valve needle and may be disposed fully or partially within the interior passage 127 of the waveguide in the open position of the valve needle.

As illustrated best in FIG. 7, the cross-sectional dimension (e.g., the diameter in the illustrated embodiment) of the portion of the valve needle 53 extending within the interior passage 127 of the waveguide 121 is sized slightly smaller than the cross-sectional dimension of the interior passage of the waveguide to define in part the flow path for high pressure fuel within the housing, and more suitably define a part of the flow path that extends between the inner surface of the waveguide sidewall 125 and the valve needle along the length of the valve needle. For example, in one embodiment the valve needle 53 is transversely spaced (e.g., radially spaced in the illustrated embodiment) from the inner surface of the waveguide sidewall 125 within the interior passage 127 of the waveguide in the range of about 0.0005 inches (0.013 mm) to about 0.0025 inches (0.064 mm).

Along a pair of longitudinally spaced segments (e.g., one segment 137 (FIG. 7) being adjacent the terminal end 123 of the waveguide 121 and the other segment 139 (FIG. **6*a*) being adjacent and just above the mounting member 79) of the valve needle 53 within the passage 127, the cross-sectional dimension of the valve needle 53 is increased so that the valve needle is in a more closely spaced or even sliding contact relationship with the waveguide within the passage to facilitate proper alignment therein and to inhibit transverse movement of the valve needle within the passage. The outer surface of the valve needle 53 at these segments has one or more flats (not shown) formed therein to in part define the portion of the flow path that extends within the interior passage 127 of the waveguide 121. Alternatively, the valve needle 53 outer surface may be longitudinally fluted at these segments to permit fuel to flow within the interior passage 127 of the waveguide 121** past such segments.

With particular reference to FIG. 7, the outer surface of the waveguide sidewall 125 is spaced transversely from the main body 25 and nozzle 27 to further define the flow path along which high pressure fuel flows from the fuel inlet 57 to the exhaust ports 83, and more suitably forms a portion of the flow path exterior, or outward of the waveguide 121. In general, the outer cross-sectional dimension (e.g., outer diameter in the illustrated embodiment) of the waveguide sidewall 125 is uniform along a length thereof intermediate an enlarged portion 195 of the waveguide disposed longitudinally at and/or adjacent the terminal end 123 of the waveguide 121, and another enlarged portion 153 disposed longitudinally adjacent the upper end 129 of the waveguide. As an example, the transverse (e.g., radial in the illustrated embodiment) spacing between the waveguide sidewall 125 and the nozzle 27 upstream (e.g., relative to the direction in which fuel flows from the upper end 33 of the nozzle to the exhaust ports 83) of the terminal end 123 of the waveguide is suitably in the range of about 0.001 inches (0.025 mm) to about 0.021 inches (0.533 mm). However, the spacing may be less than or greater than that without departing from the scope of this invention.

The outer cross-sectional dimension of the portion 195 of the lower segment 133 of the waveguide 121 suitably increases, and more suitably tapers or flares transversely outward adjacent to or more suitably at the terminal end 123 of the waveguide. For example, the cross-sectional dimension of this enlarged portion 195 of the lower segment 133 of the waveguide 121 is sized for closely spaced or even sliding contact relationship with the nozzle 27 within the central bore 75 thereof to maintain proper axial alignment of the waveguide (and hence the valve needle 53) within the high pressure chamber 55.

As a result, the portion of the flow path between the waveguide 121 and the nozzle 27 is generally narrower adjacent to or at the terminal end 123 of the waveguide relative to the flow path immediately upstream of the terminal end of the waveguide to generally restrict the flow of fuel past the terminal end of the waveguide to the exhaust ports 83. The enlarged portion 195 of the lower segment 133 of the waveguide 121 also provides increased ultrasonically excited surface area to which the fuel flowing past the terminal end 123 of the waveguide is exposed. One or more flats 197 (FIG. 9) are formed in the outer surface of the enlarged portion 195 of the lower segment 133 to facilitate the flow of fuel along the flow path past the terminal end 123 of the waveguide 121 for flow to the exhaust ports 83 of the nozzle 27. It is understood that the enlarged portion 195 of the waveguide sidewall 115 may be stepped outward instead of tapered or flared. It is also contemplated the upper and lower surfaces of the enlarged portion 195 may be contoured instead of straight and remain within the scope of this invention.

In one example, the enlarged portion 195 of the waveguide lower segment 133, e.g., at and/or adjacent the terminal end 123 of the waveguide, has a maximum outer cross-sectional dimension (e.g., outer diameter in the illustrated embodiment) of about 0.2105 inches (5.35 mm), whereas the maximum outer cross-sectional dimension of the waveguide immediately upstream of this enlarged portion may be in the range of about 0.16 inches (4.06 mm) to slightly less than about 0.2105 inches (5.35 mm).

The transverse spacing between the terminal end 123 of the waveguide 121 and the nozzle 27 defines an open area through which fuel flows along the flow path past the terminal end of the waveguide. The one or more exhaust ports 83 define an open area through which fuel exits the housing 23. For example, where one exhaust port is provided the open area through which fuel exits the housing 23 is defined as the cross-sectional area of the exhaust port (e.g., where fuel enters into the exhaust port) and where multiple exhaust ports 83 are present the open area through which fuel exits the housing is defined as the sum of the cross-sectional area of each exhaust port. In one embodiment, a ratio of the open area at the terminal end 123 of the waveguide 121 and the nozzle 27 to the open area through which fuel exits the housing 23 (e.g. at exhaust ports 83) is suitably in the range of about 4:1 to about 20:1.

It is understood that in other suitable embodiments the lower segment 133 of the waveguide 121 may have a generally uniform outer cross-sectional dimension along its entire length (e.g. such that no enlarged portion 195 is formed), or may decrease in outer cross-sectional dimension (e.g., substantially narrow towards its terminal end 123) without departing from the scope of the invention.

Referring again to FIGS. 8 and 9, an excitation device adapted to energize the waveguide 121 to mechanically vibrate ultrasonically is suitably disposed entirely within the high pressure chamber 55 along with the waveguide and is generally indicated at 145. In one embodiment, the excitation device 145 is suitably responsive to high frequency (e.g., ultrasonic frequency) electrical current to vibrate the waveguide ultrasonically. As an example, the excitation device 145 may suitably receive high frequency electrical current from a suitable generating system (not shown) that is operable to deliver high frequency alternating current to the excitation device. The term "ultrasonic" as used herein is taken to mean having a frequency in the range of about 15 kHz to about 100 kHz. As an example, in one embodiment the generating system may suitably deliver alternating current to the excitation device at an ultrasonic frequency in the range of about 15 kHz to about 100 kHz, more suitably in the range of about 15 kHz to about 60 kHz, and even more suitably in the range of about 20 kHz to about 40 kHz. Such generating systems are well known to those skilled in the art and need not be further described herein.

In the illustrated embodiment the excitation device 145 comprises a piezoelectric device, and more suitably a plurality of stacked piezoelectric rings 147 (e.g., at least two and in the illustrated embodiment four) surrounding the upper segment 131 of the waveguide 121 and seated on a shoulder 149 formed by the mounting member 79. An annular collar 151 surrounds the upper segment 131 of the waveguide 121 above the piezoelectric rings 147 and bears down against the uppermost ring. Suitably, the collar 151 is constructed of a high density material. For example, one suitable material from which the collar 151 may be constructed is tungsten. It is understood, however, that the collar 151 may be constructed of other suitable materials and remain within the scope of this invention. The enlarged portion 153 adjacent the upper end 129 of the waveguide 121 has an increased outer cross-sectional dimension (e.g., an increased outer diameter in the illustrated embodiment) and is threaded along this segment. The collar 151 is internally threaded to threadably fasten the collar on the waveguide 121. The collar 151 is suitably tightened down against the stack of piezoelectric rings 147 to compress the rings between the collar and the shoulder 149 of the mounting member 79.

The waveguide 121 and excitation device 145 of the illustrated embodiment together broadly define a waveguide assembly, indicated generally at 150, for ultrasonically energizing the fuel in the high pressure chamber 55. Accordingly, the entire waveguide assembly 150 is disposed entirely within the high pressure fuel chamber 55 of the fuel injector 21 and is thus generally uniformly exposed to the high pressure environment within the fuel injector. As an example, the illustrated waveguide assembly is particularly constructed to act as both an ultrasonic horn and a transducer to ultrasonically vibrate the ultrasonic horn. In particular, the lower segment 133 of the waveguide 121 as illustrated in FIG. 8 generally acts in the manner of an ultrasonic horn while the upper segment 131 of the waveguide, and more suitably the portion of the upper segment that extends generally from the mounting member 79 to the location at which the collar 151 fastens to the upper segment of the waveguide together with the excitation device (e.g., the piezoelectric rings) acts in the manner of a transducer.

Upon delivering electrical current (e.g., alternating current delivered at an ultrasonic frequency) to the piezoelectric rings 147 of the illustrated embodiment the piezoelectric rings expand and contract (particularly in the longitudinal direction of the fuel injector 21) at the ultrasonic frequency at which current is delivered to the rings. Because the rings 147 are compressed between the collar 151 (which is fastened to the upper segment 131 of the waveguide 21) and the mounting member 79, expansion and contraction of the rings causes the upper segment of the waveguide to elongate and contract ultrasonically (e.g., generally at the frequency that the piezoelectric rings expand and contract), such as in the manner of a transducer. Elongation and contraction of the upper segment 131 of the waveguide 121 in this manner excites the resonant frequency of the waveguide, and in particular along the lower segment 133 of the waveguide, resulting in ultrasonic vibration of the waveguide along the lower segment, e.g., in the manner of an ultrasonic horn.

As an example, in one embodiment the displacement of the lower segment 133 of the waveguide 121 resulting from ultrasonic excitation thereof may be up to about six times the displacement of the piezoelectric rings and upper segment of the waveguide. It is understood, though, that the displacement of the lower segment 133 may be amplified more than six times, or it may not be amplified at all, and remain within the scope of this invention.

It is contemplated that a portion of the waveguide 121 (e.g., a portion of the upper segment 131 of the waveguide) may alternatively be constructed of a magnetostrictive material that is responsive to magnetic fields changing at ultrasonic frequencies. In such an embodiment (not shown) the excitation device may comprise a magnetic field generator disposed in whole or in part within the housing 23 and operable in response to receiving electrical current to apply a magnetic field to the magnetostrictive material wherein the magnetic field changes at ultrasonic frequencies (e.g., from on to off, from one magnitude to another, and/or a change in direction).

For example a suitable generator may comprise an electrical coil connected to the generating system which delivers current to the coil at ultrasonic frequencies. The magnetostrictive portion of the waveguide and the magnetic field generator of such an embodiment thus together act as a transducer while the lower segment 133 of the waveguide 121 again acts as an ultrasonic horn. One example of a suitable magnetostrictive material and magnetic field generator is disclosed in U.S. Pat. No. 6,543,700, the disclosure of which is incorporated herein by reference to the extent it is consistent herewith.

While the entire waveguide assembly 150 is illustrated as being disposed within the high pressure chamber 55 of the fuel injector housing 23, it is understood that one or more components of the waveguide assembly may be wholly or partially disposed exterior of the high pressure chamber, and may even be disposed exterior of the housing, without departing from the scope of this invention. For example, where a magnetostrictive material is used, the magnetic field generator (broadly, the excitation device) may be disposed in the main body 25 or other component of the fuel injector housing 23 and be only partially exposed to or completely sealed off from the high pressure chamber 55. In another embodiment, the upper segment 131 of the waveguide 121 and the piezoelectric rings 147 (and collar 151) may together be located exterior of the high pressure chamber 55 without departing from the scope of this invention, as long as the terminal end 123 of the waveguide is disposed within the high pressure chamber.

By placing the piezoelectric rings 147 and collar 151 about the upper segment 131 of the waveguide 121, the entire waveguide assembly 150 need be no longer than the waveguide itself (e.g., as opposed to the length of an assembly in which a transducer and ultrasonic horn are arranged in a conventional end-to-end, or "stacked" arrangement). As one example, the overall waveguide assembly 150 may suitably have a length equal to about one-half of the resonating wavelength (otherwise commonly referred to as one-half wavelength) of the waveguide. In particular, the waveguide assembly 150 is suitably configured to resonate at an ultrasonic frequency in the range of about 15 kHz to about 100 kHz, more suitably in the range of about 15 kHz to about 60 kHz, and even more suitably in the range of about 20 kHz to about 40 kHz. The one-half wavelength waveguide assembly 150 operating at such frequencies has a respective overall length (corresponding to a one-half wavelength) in the range of about 133 mm to about 20 mm, more suitably in the range of about 133 mm to about 37.5 mm and even more suitably in the range of about 100 mm to about 50 mm. As a more particular example, the waveguide assembly 150 illustrated in FIGS. 8 and 9 is configured for operation at a frequency of about 40 kHz and has an overall length of about 50 mm. It is understood, however, that the housing 23 may be sufficiently sized to permit a waveguide assembly having a full wavelength to be disposed therein. It is also understood that in such an arrangement the waveguide assembly may comprise an ultrasonic horn and transducer in a stacked configuration.

An electrically non-conductive sleeve 155 (which is cylindrical in the illustrated embodiment but may be shaped otherwise) is seated on the upper end of the collar 151 and extends up from the collar to the upper end of the high pressure chamber 55. The sleeve 155 is also suitably constructed of a generally flexible material. As an example, one suitable material from which the sleeve 155 may be constructed is an amorphous thermoplastic polyetherimide material available from General Electric Company, U.S.A., under the tradename ULTEM. However, other suitable electrically non-conductive materials, such as ceramic materials, may be used to construct the sleeve 155 and remain within the scope of this invention. The upper end of the sleeve 155 has an integrally formed annular flange 157 extending radially outward therefrom, and a set of four longitudinally extending slots 159 defining four generally flexible tabs 161 at the upper end of the sleeve. A second annular flange 163 is formed integrally with the sleeve 155 and extends radially outward from the sleeve just below the longitudinally extending slots 159, i.e., in longitudinally spaced relationship with the annular flange 157 disposed at the upper end of the sleeve.

A contact ring 165 constructed of an electrically conductive material circumscribes the sleeve 155 intermediate the longitudinally spaced annular flanges 157, 163 of the sleeve.

In one embodiment, the contact ring 165 is suitably constructed of brass. It is understood, however, that the contact ring 165 may be constructed of other suitable electrically conductive materials without departing from the scope of this invention. It also understood that a contact device other than a ring, such as a single point contact device, flexible and/or spring-loaded tab or other suitable electrically conductive device, may be used without departing from the scope of the invention. In the illustrated embodiment, the inner cross-sectional dimension (e.g., the diameter) of the contact ring 165 is sized slightly smaller than the outer cross-sectional dimension of the longitudinal segment of the sleeve 155 extending between the annular flanges 157, 163.

The contact ring 165 is inserted onto the sleeve 155 by urging the contact ring telescopically down over the upper end of the sleeve. The force of the ring 165 against the annular flange 157 at the upper end of the sleeve 155 urges the tabs 161 to flex (e.g. bend) radially inward to allow the ring to slide down past the annular flange formed at the upper end of the sleeve and to seat the ring on the second annular flange 163. The tabs 161 resiliently move back out toward their initial position, providing frictional engagement between the contact ring 165 and the sleeve 155 and retaining the contact ring between the annular flanges 157, 163 of the sleeve.

A guide ring 167 constructed of an electrically non-conductive material circumscribes and electrically insulates the contact ring 165. As an example, the guide ring 167 may (but need not necessarily) be constructed of the same material as the sleeve 163. In one embodiment, the guide ring 167 is suitably retained on the sleeve, and more suitably on the contact ring 165, by a clamping, or frictional fit of the guide ring on the contact ring. For example, the guide ring 167 may be a discontinuous ring broken along a slot as illustrated in FIG. 9. The guide ring 167 is thus circumferentially expandable at the slot to fit the guide ring over the contact ring 165 and upon subsequent release closes resiliently and securely around the contact ring.

In one particularly suitable embodiment, an annular locating nub 169 extends radially inward from the guide ring 167 and is receivable in an annular groove 171 formed in the contact ring 165 to properly locate the guide ring on the contact ring. It is understood, however, that the contact ring 165 and guide ring 167 may be mounted on the sleeve 155 other than as illustrated in FIGS. 8 and 9 without departing from the scope of this invention. At least one, and more suitably a plurality of tapered or frusto-conically shaped openings 173 are formed radially through the guide ring 167 to permit access to the contact ring 165 for delivering electrical current to the contact ring.

Figure 5:
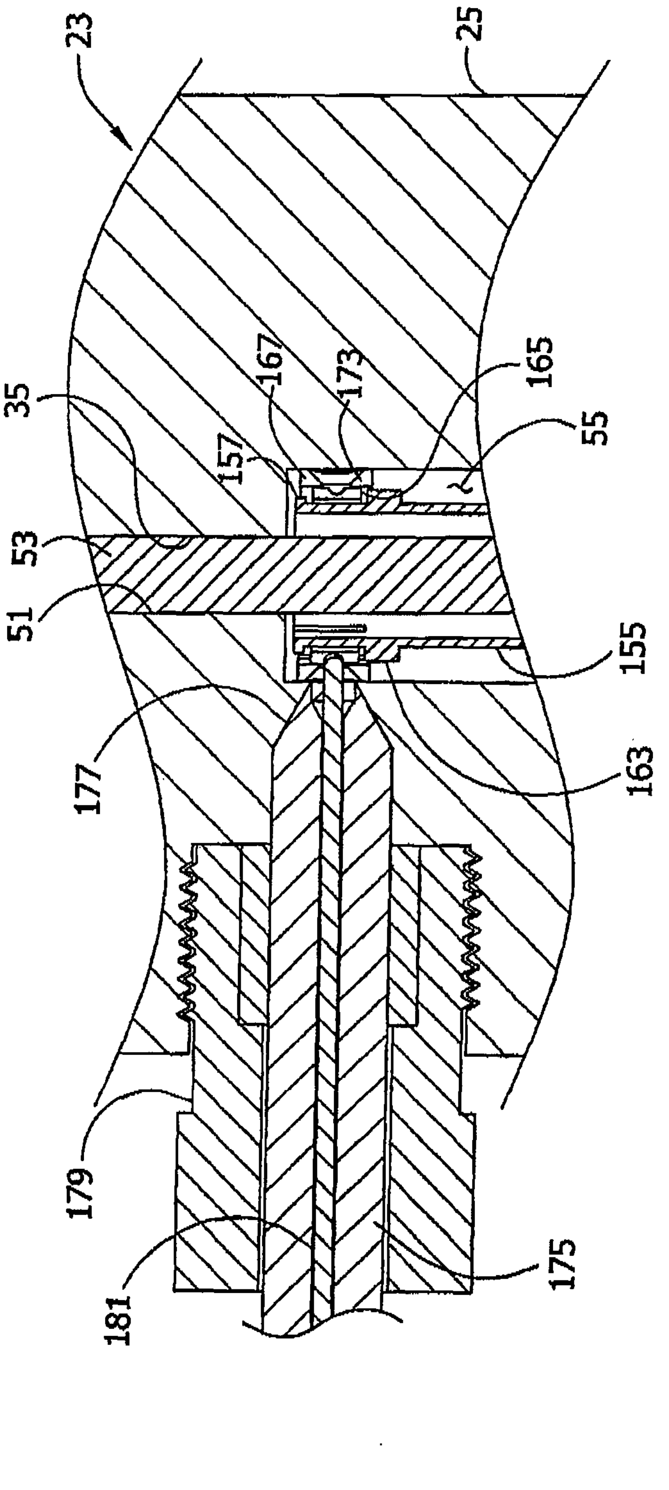
FIG. 5 is an expanded view of a third portion of the cross-section of FIG. 2.

As seen best in FIG. 5, an insulating sleeve 175 constructed of a suitable electrically non-conductive material extends through an opening in the side of the main body 25 and has a generally conically shaped terminal end 177 configured to seat within one of the openings 173 of the guide ring 167. The insulating sleeve 175 is held in place by a suitable fitting 179 that threadably fastens to the main body 25 within the opening 173 and has a central opening through which the insulating sleeve extends. Suitable electrical wiring 181 extends through the insulating sleeve 175 into electrical contact with the contact ring 165 at one end of the wire and is in electrical communication at its opposite end (not shown) with a source (not shown) of electrical current.

Additional electrical wiring 183 extends from the contact ring 165 down along the outside of the sleeve 155 within the high pressure chamber 55 and into electrical communication with an electrode (not shown) disposed between the uppermost piezoelectric ring 147 and the next lower piezoelectric ring. A separate wire 184 electrically connects the electrode to another electrode (not shown) disposed between the lowermost piezoelectric ring 147 and the ring just above it. The mounting member 79 and/or the waveguide 121 provide the ground for the current delivered to the piezoelectric rings 147. In particular, a ground wire 185 is connected to the mounting member 79 and extends up to between the middle two piezoelectric rings 147 into contact with an electrode (not shown) disposed therebetween. Optionally, a second ground wire (not shown) may extend from between the middle two piezoelectric rings 147 into contact with another electrode (not shown) between the uppermost piezoelectric ring and the collar 151.

With particular reference now to FIGS. 6, **6*a*, 8 and 9, the mounting member 79 is suitably connected to the waveguide 121 intermediate the ends 123, 129 of the waveguide. More suitably, the mounting member 79 is connected to the waveguide 121 at a nodal region of the waveguide. As used herein, the "nodal region" of the waveguide 121 refers to a longitudinal region or segment of the waveguide along which little (or no) longitudinal displacement occurs during ultrasonic vibration of the waveguide and transverse (e.g., radial in the illustrated embodiment) displacement is generally maximized. Transverse displacement of the waveguide 121** suitably comprises transverse expansion of the waveguide but may also include transverse movement (e.g., bending) of the waveguide.

In the illustrated embodiment, the configuration of the waveguide 121 is such that a nodal plane (i.e., a plane transverse to the waveguide at which no longitudinal displacement occurs while transverse displacement is generally maximized) is not present. Rather, the nodal region of the illustrated waveguide 121 is generally dome-shaped such that at any given longitudinal location within the nodal region some longitudinal displacement may still be present while the primary displacement of the waveguide is transverse displacement.

It is understood, however, that the waveguide 121 may be suitably configured to have a nodal plane (or nodal point as it is sometimes referred to) and that the nodal plane of such a waveguide is considered to be within the meaning of nodal region as defined herein. It is also contemplated that the mounting member 79 may be disposed longitudinally above or below the nodal region of the waveguide 121 without departing from the scope of the invention.

The mounting member 79 is suitably configured and arranged in the fuel injector 21 to vibrationally isolate the waveguide 121 from the fuel injector housing 23. That is, the mounting member 25 inhibits the transfer of longitudinal and transverse (e.g., radial) mechanical vibration of the waveguide 121 to the fuel injector housing 23 while maintaining the desired transverse position of the waveguide within the high pressure chamber 55 and allowing longitudinal displacement of the waveguide within the fuel injector housing. As one example, the mounting member 79 of the illustrated embodiment generally comprises an annular inner segment 187 extending transversely (e.g., radially in the illustrated embodiment) outward from the waveguide 121, an annular outer segment 189 extending transverse to the waveguide in transversely spaced relationship with the inner segment, and an annular interconnecting web 191 extending transversely between and interconnecting the inner and outer segments. While the inner and outer segments 187, 189 and interconnecting web 191 extend continuously about the circumference of the waveguide 121, it is understood that one or more of these elements may be discontinuous about the waveguide such as in the manner of wheel spokes, without departing from the scope of this invention.

Figure 6A:
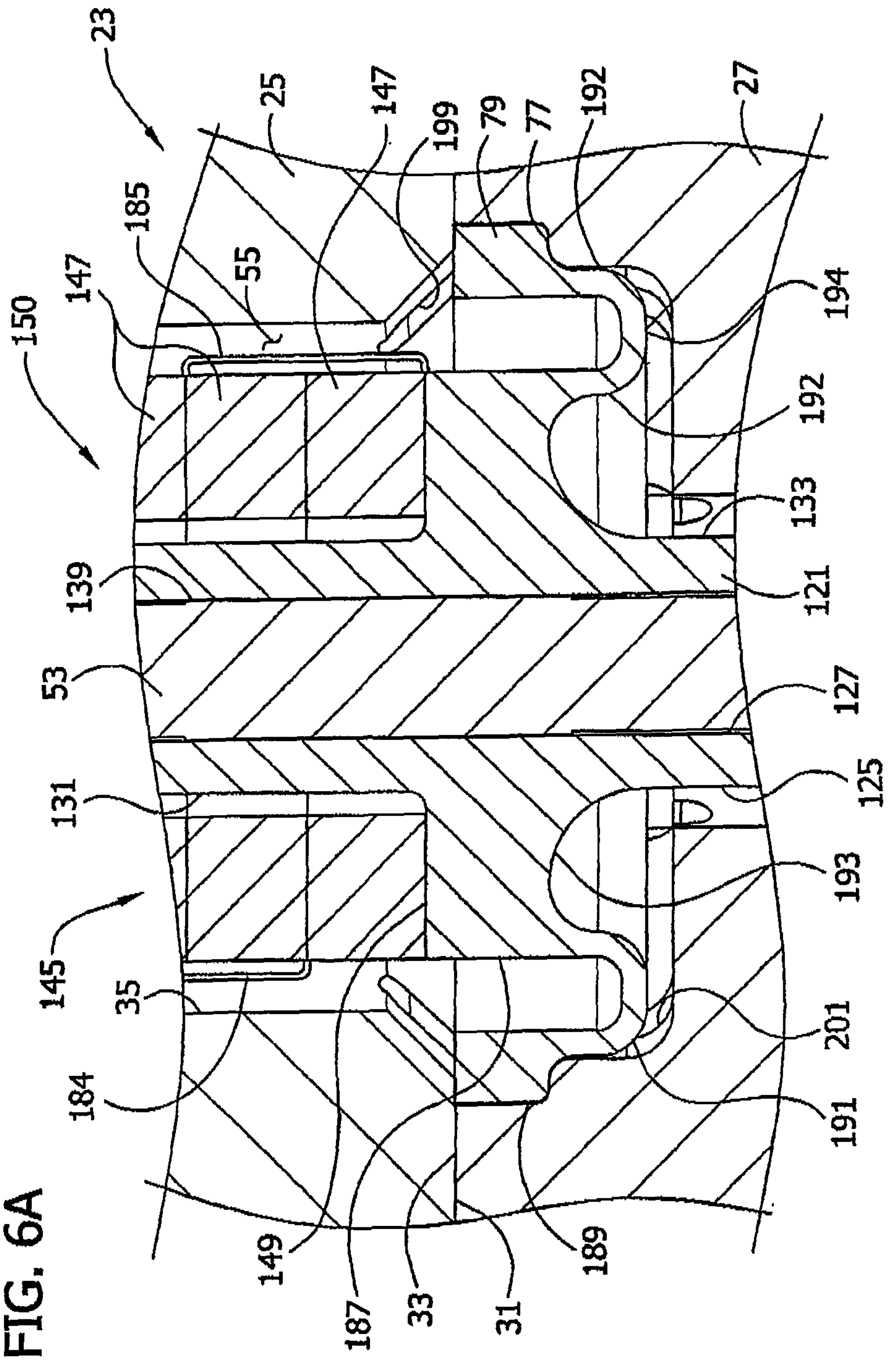
FIG. 6*a* is an expanded view of a central portion of the cross-section of FIG. 1.

In the embodiment illustrated in FIG. 6*a*, the inner segment 187 of the mounting member 79 has a generally flat upper surface that defines the shoulder 149 on which the excitation device 145, e.g., the piezoelectric rings 147, is seated. A lower surface 193 of the inner segment 187 is suitably contoured as it extends from adjacent the waveguide 121 to its connection with the interconnecting web 191, and more suitably has a blended radius contour. In particular, the contour of the lower surface 193 at the juncture of the web 191 and the inner segment 187 of the mounting member 79 is suitably a smaller radius (e.g., a sharper, less tapered or more corner-like) contour to facilitate distortion of the web during vibration of the waveguide 121. The contour of the lower surface 193 at the juncture of the inner segment 187 of the mounting member 79 and the waveguide 121 is suitably a relatively larger radius (e.g., a more tapered or smooth) contour to reduce stress in the inner segment of the mounting member upon distortion of the interconnecting web 191 during vibration of the waveguide.

The outer segment 189 of the mounting member 79 is configured to seat down against a shoulder formed by the nozzle 27 generally adjacent the upper end 33 of the nozzle. As seen best in FIG. 6, the internal cross-sectional dimension (e.g., internal diameter) of the nozzle 27 is stepped inward adjacent the upper end 33 of the nozzle, e.g., longitudinally below the mounting member 79, so that that nozzle is longitudinally spaced from the contoured lower surface 193 of the inner segment 187 and interconnecting web 191 of the mounting member to allow for displacement of the mounting member during ultrasonic vibration of the waveguide 121. The mounting member 79 is suitably sized in transverse cross-section so that at least an outer edge margin of the outer segment 189 is disposed longitudinally between the shoulder of the nozzle 27 and the lower end 31 of the main body 25 of the fuel injector housing 23 (i.e., the surface of the main body that seats against the upper end 33 of the nozzle). The retaining member 29 of the fuel injector 21 urges the nozzle 27 and the main body 25 together to secure the edge margin of the mounting member outer segment 189 therebetween.

The interconnecting web 191 is constructed to be relatively thinner than the inner and outer segments 187, 189 of the mounting member 79 to facilitate flexing and/or bending of the web in response to ultrasonic vibration of the waveguide 121. As an example, in one embodiment the thickness of the interconnecting web 191 of the mounting member 79 may be in the range of about 0.2 mm to about 1 mm, and more suitably about 0.4 mm. The interconnecting web 191 of the mounting member 79 suitably comprises at least one axial component 192 and at least one transverse (e.g., radial in the illustrated embodiment) component 194. In the illustrated embodiment, the interconnecting web 191 has a pair of transversely spaced axial components 192 connected by the transverse component 194 such that the web is generally U-shaped in cross-section.

It is understood, however, that other configurations that have at least one axial component 192 and at least one transverse component 194 are suitable, such as L-shaped, H-shaped, I-shaped, inverted U-shaped, inverted L-shaped, and the like, without departing from the scope of this invention. Additional examples of suitable interconnecting web 191 configurations are illustrated and described in U.S. Pat. No. 6,676,003, the disclosure of which is incorporated herein by reference to the extent it is consistent herewith.

The axial components 192 of the web 191 depend from the respective inner and outer segments 187, 189 of the mounting member and are generally cantilevered to the transverse component 194. Accordingly, the axial component 192 is capable of dynamically bending and/or flexing relative to the outer segment 189 of the mounting member in response to transverse vibratory displacement of the inner segment 187 of the mounting member to thereby isolate the housing 23 from transverse displacement of the waveguide. The transverse component 194 of the web 191 is cantilevered to the axial components 192 such that the transverse component is capable of dynamically bending and flexing relative to the axial components (and hence relative to the outer segment 189 of the mounting member) in response to axial vibratory displacement of the inner segment 187 to thereby isolate the housing 23 from axial displacement of the waveguide.

In the illustrated embodiment, the waveguide 121 expands radially as well as displaces slightly axially at the nodal region (e.g., where the mounting member 79 is connected to the waveguide) upon ultrasonic excitation of the waveguide. In response, the U-shaped interconnecting member 191 (e.g., the axial and transverse components 192, 194 thereof) generally bends and flexes, and more particularly rolls relative to the fixed outer segment 189 of the mounting member 79, e.g., similar to the manner in which a toilet plunger head rolls upon axial displacement of the plunger handle. Accordingly, the interconnecting web 79 isolates the fuel injector housing 23 from ultrasonic vibration of the waveguide 121, and in the illustrated embodiment it more particularly isolates the outer segment 189 of the mounting member from vibratory displacement of the inner segment 187 thereof. Such a mounting member 79 configuration also provides sufficient bandwidth to compensate for nodal region shifts that can occur during ordinary operation. In particular, the mounting member 79 can compensate for changes in the real time location of the nodal region that arise during the actual transfer of ultrasonic energy through the waveguide 121. Such changes or shifts can occur, for example, due to changes in temperature and/or other environmental conditions within the high pressure chamber 55.

While in the illustrated embodiment the inner and outer segments 187, 189 of the mounting member 79 are disposed generally at the same longitudinal location relative to the waveguide, it is understood that the inner and outer segments may be longitudinally offset from each other without departing from the scope of this invention. It is also contemplated that the interconnecting web 191 may comprise only one or more axial components 192 (e.g., the transverse component 194 may be omitted) and remain within the scope of this invention. For example where the waveguide 121 has a nodal plane and the mounting member 79 is located on the nodal plane, the mounting member need only be configured to isolate the transverse displacement of the waveguide. In an alternative embodiment (not shown), it is contemplated that the mounting member may be disposed at or adjacent an anti-nodal region of the waveguide, such as at one of the opposite ends 123, 129 of the waveguide. In such an embodiment, the interconnecting web 191 may comprise only one or more transverse components 194 to isolate axial displacement of the waveguide (i.e., little or no transverse displacement occurs at the anti-nodal region).

In one particularly suitable embodiment the mounting member 79 is of single piece construction. Even more suitably the mounting member 79 may be formed integrally with the waveguide 121 as illustrated in FIG. 6. However, it is understood that the mounting member 79 may be constructed separate from the waveguide 121 and remain within the scope of this invention. It is also understood that one or more components of the mounting member 79 may be separately constructed and suitably connected or otherwise assembled together.

In one suitable embodiment the mounting member 79 is further constructed to be generally rigid (e.g., resistant to static displacement under load) so as to hold the waveguide 121 (and hence the valve needle 53) in proper alignment within the high pressure chamber 55. For example, the rigid mounting member in one embodiment may be constructed of a non-elastomeric material, more suitably metal, and even more suitably the same metal from which the waveguide is constructed. The term rigid is not, however, intended to mean that the mounting member is incapable of dynamic flexing and/or bending in response to ultrasonic vibration of the waveguide. In other embodiments, the rigid mounting member may be constructed of an elastomeric material that is sufficiently resistant to static displacement under load but is otherwise capable of dynamic flexing and/or bending in response to ultrasonic vibration of the waveguide. While the mounting member 79 illustrated in FIG. 6 is constructed of a metal, and more suitably constructed of the same material as the waveguide 121, it is contemplated that the mounting member may be constructed of other suitable generally rigid materials without departing from the scope of this invention.

With reference back to FIGS. 6 and 8, the flow path along which fuel flows within the high pressure chamber 55 of the fuel injector housing 23 is defined in part by the transverse spacing between the inner surface of the nozzle 27 and the outer surface of the lower segment 133 of the waveguide 121 (e.g., below the mounting member 79), and between the inner surface of the main body 25 and the outer surfaces of the excitation device 145, the collar 151 and the sleeve 155 (e.g. above the mounting member). The fuel flow path is in fluid communication with the fuel inlet 57 of the main body 25 of the injector housing 23 generally at the sleeve 155 such that high pressure fuel entering the flow path from the fuel inlet flows down (in the illustrated embodiment) along the flow path toward the nozzle tip 81 for exhaustion from the nozzle 27 via the exhaust ports 83. As described previously, additional high pressure fuel flows within the interior passage 127 of the waveguide 121 between the waveguide and the valve needle 53.

Figure 10:
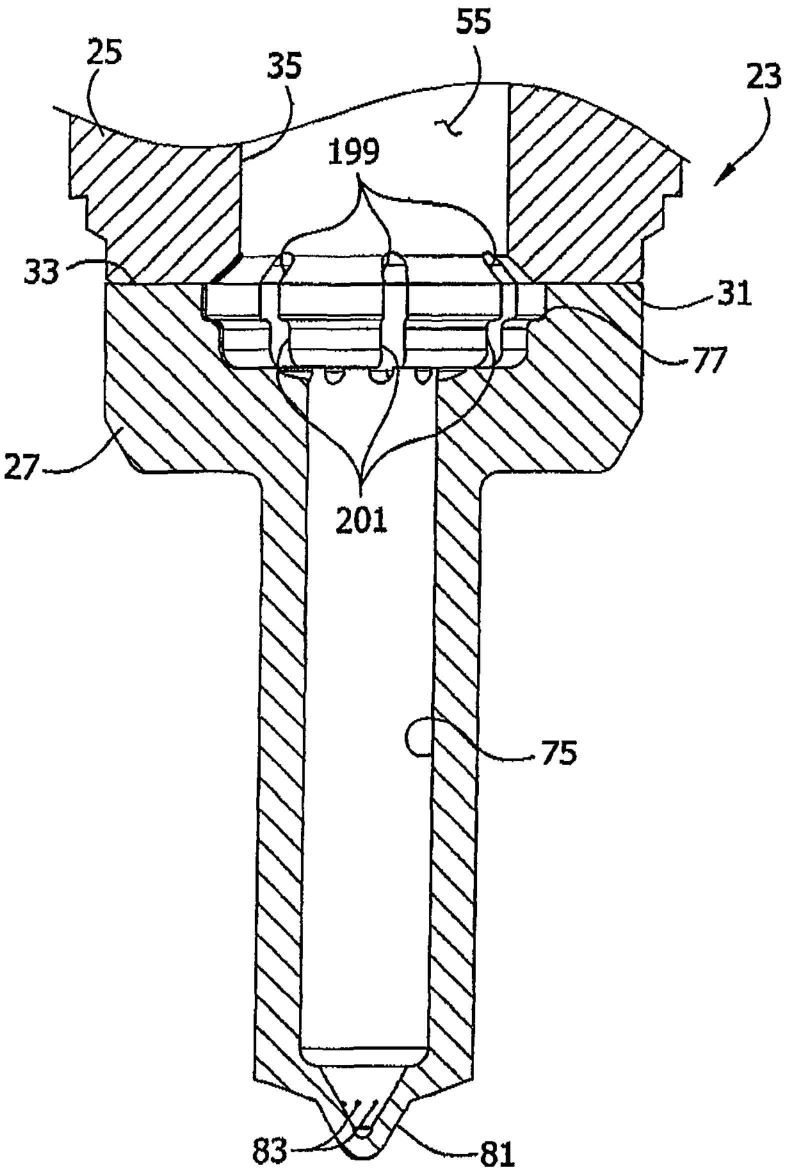
FIG. 10 is a fragmented cross-section of a portion of a fuel injector housing of the fuel injector of FIG. 1, with internal components of the fuel injector omitted to reveal construction of the housing.

Because the mounting member 79 extends transverse to the waveguide 121 within the high pressure chamber 55, the lower end 31 of the main body 25 and the upper end 33 of the nozzle 27 are suitably configured to allow the fuel flow path to divert generally around the mounting member as fuel flows within the high pressure chamber. For example, as best illustrated in FIG. 10, suitable channels 199 are formed in the lower end 31 of the main body 25 in fluid communication with the flow path upstream of the mounting member 79 and are aligned with respective channels 201 formed in the upper end 33 of the nozzle 27 in fluid communication with the flow path downstream of the mounting member. Accordingly, high pressure fuel flowing from the fuel inlet 57 down along the flow path upstream of the mounting member 79 (e.g., between the main body 25 and the sleeve 155/collar 151/piezoelectric rings 147) is routed through the channels 199 in the main body around the mounting member and through the channels 201 in the nozzle 27 to the flow path downstream of the mounting member (e.g., between the nozzle and the waveguide 121).

In one embodiment, the fuel injector is operated by a suitable control system (not shown) to control operation of the solenoid valve and operation of the excitation device 145. Such control systems are known to those skilled in the art and need not be described further herein except to the extent necessary. Unless an injection operation is occurring, the valve needle 53 is biased by the spring 111 in the bore 35 of the main body 25 to its closed position with the terminal end 115 of the valve needle in sealing contact with the nozzle tip 81 to close the exhaust ports 83. The solenoid valve provides a closure at the recess 95 formed in the head 87 of the pin holder 47 to close the bore 97 that extends longitudinally through the pin holder. No current is supplied by the control system to the waveguide assembly in the closed position of the valve needle 53.

High pressure fuel flows from a source of fuel (not shown) into the fuel injector 21 at the fuel inlet 57 of the housing 23. Suitable fuel delivery systems for delivering pressurized fuel from the fuel source to the fuel injector 21 are known in the art and need not be further described herein. In one embodiment, the high pressure fuel may be delivered to the fuel injector 21 at a pressure in the range of about 8,000 psi (550 bar) to about 30,000 psi (2070 bar). The high pressure fuel flows through the upper distribution channel 59 of the main body 25 to the annular gap 99 between the main body and the pin holder 47, and through the feed channel 101 of the pin holder into the internal channel 91 of the pin holder above the pin 93 and up through the bore 97 in the pin holder. High pressure fuel also flows through the high pressure flow path, i.e., through the lower distribution channel 61 of the main body 25 to the high pressure chamber 55 to fill the high pressure chamber, both outward of the waveguide 121 and within the interior passage 127 of the waveguide. In this condition the high pressure fuel above the pin 93, together with the bias of the spring 111, inhibits the high pressure fuel in the high pressure chamber 55 against urging the valve needle 53 to its open position.

When the injector control system determines that an injection of fuel to the combustion engine is needed, the solenoid valve is energized by the control system to open the pin holder bore 97 so that high pressure fuel flows out from the pin holder to the fuel return channel 71 at the upper end 37 of the main body 25 as lower pressure fuel, thereby decreasing the fuel pressure behind (e.g., above) the pin 93 within the pin holder. Accordingly, the high pressure fuel in the high pressure chamber 55 is now capable of urging the valve needle 53 against the bias of the spring 111 to the open position of the valve needle. In the open position of the valve needle 53, the terminal end 115 of the valve needle is sufficiently spaced from the nozzle tip 81 at the exhaust ports 83 to permit fuel in the high pressure chamber 55 to be exhausted through the exhaust ports.

Upon energizing the solenoid valve to allow the valve needle 53 to move to its open position, such as approximately concurrently therewith, the control system also directs the high frequency electrical current generator to deliver current to the excitation device 145, i.e., the piezoelectric rings 147 in the illustrated embodiment, via the contact ring 165 and suitable wiring 183 that electrically connects the contact ring to the piezoelectric rings. As described previously, the piezoelectric rings 147 are caused to expand and contract (particularly in the longitudinal direction of the fuel injector 21) generally at the ultrasonic frequency at which current is delivered to the excitation device 145.

Expansion and contraction of the rings 147 causes the upper segment 131 of the waveguide 121 to elongate and contract ultrasonically (e.g., generally at the same frequency that the piezoelectric rings expand and contract). Elongation and contraction of the upper segment 131 of the waveguide 121 in this manner excites the waveguide (e.g., suitably at the resonant frequency of the waveguide), and in particular along the lower segment 133 of the waveguide, resulting in ultrasonic vibration of the waveguide along the lower segment and in particular at the expanded portion 195 of the lower segment at the terminal end 123 thereof.

With the valve needle 53 in its open position, high pressure fuel in the high pressure chamber 55 flows along the flow path, and in particular past the ultrasonically vibrating terminal end 123 of the waveguide 121, to the exhaust ports 83 of the nozzle tip 81. Ultrasonic energy is applied by the terminal end 123 of the waveguide 121 to the high pressure fuel just upstream (along the flow path) of the exhaust ports 83 to generally atomize the fuel (e.g., to decrease droplet size and narrow the droplet size distribution of the fuel exiting the injector 21). Ultrasonic energization of the fuel before it exits the exhaust ports 83 produces a pulsating, generally cone-shaped spray of atomized liquid fuel delivered into the combustion chamber served by the fuel injector 21.

In the illustrated embodiment of FIGS. 1-10 and as described previously herein, operation of the pin 93, and hence the valve needle 53, is controlled by the solenoid valve (not shown). It is understood, however, that other devices, such as, without limitation, cam actuated devices, piezoelectric or magnetostrictive operated devices, hydraulically operated devices or other suitable mechanical devices, with or without fluid amplifying valves, may be used to control operation of the valve needle without departing from the scope of this invention.

Figure 11:
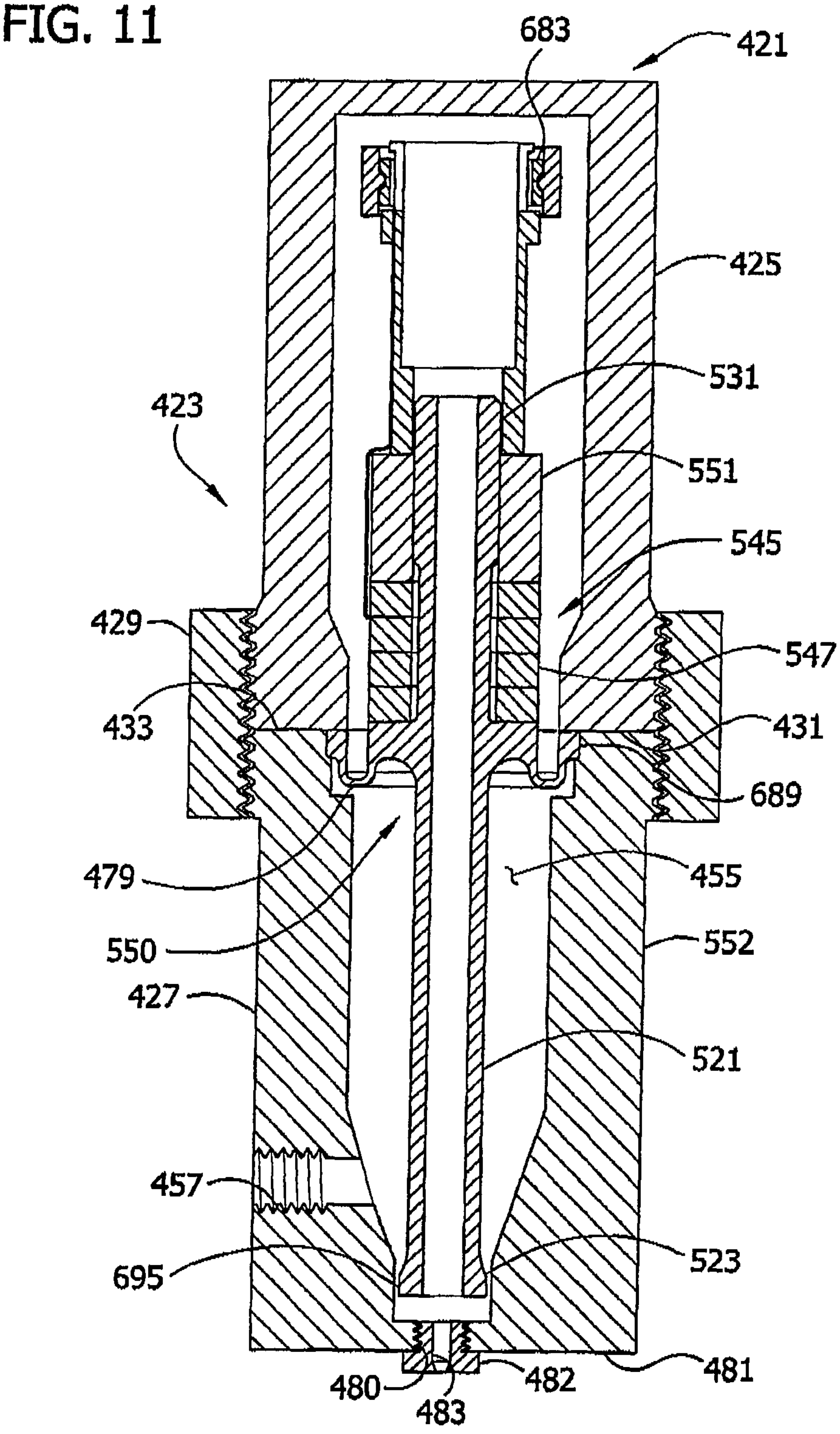
FIG. 11 is a longitudinal cross-section of an ultrasonic liquid delivery device according to a second embodiment of the present invention.

FIG. 11 illustrates a second embodiment of an ultrasonic liquid delivery device, generally indicated at 421, of the present invention. The device 421 of this second embodiment is broadly described herein with reference to any ultrasonically driven device in which a pressurized spray of liquid is exhausted from the device following application of ultrasonic energy to the liquid, it being contemplated that such a device may have application in apparatus such as, without limitation, nebulizers and other drug delivery devices, molding equipment, humidifiers, fuel injection apparatus for engines, paint spray systems, ink delivery systems, mixing systems, homogenization systems, spray drying systems, cooling systems and other applications in which an ultrasonically generated spray of liquid is utilized.

The illustrated device 421 comprises a housing, designated generally at 423, having an inlet 457 for receiving liquid into the housing. The liquid is suitably pressurized in the range of slightly above 0.0 psi (0.0 bar) to about 50,000 psi (3,450 bar). In the illustrated embodiment, the housing 423 is comprised at least in part of an upper (with respect to the vertical orientation of the device 421 illustrated in FIG. 11) housing member 425 and a lower housing member. A lower end 431 of the upper housing member 425 seats against an upper end 433 of the lower housing member 427 and the housing members are secured together by a suitable threaded connector 429. The upper and lower housing members 425, 427 together define an internal chamber 455, in fluid communication with the inlet 457. The lower housing member 427 has a axially extending threaded bore 480 formed in its bottom for threadably receiving an insert 482 therein such that the insert further defines the housing 423 of the device 421. An exhaust port 483 extends axially through the insert 482 to broadly define an exhaust port of the housing 423 through which liquid is exhausted from the housing.

While the insert 482 illustrated in FIG. 11 has a single exhaust port 483, it is contemplated that the insert may comprise more than one exhaust port. It is also contemplated that the insert 482 may be omitted altogether and the bottom of the lower housing member 427 generally closed with one or more exhaust ports formed therein. The housing 423 of the illustrated embodiment is generally cylindrical but may suitably be of any shape, and may be sized depending at least in part on the desired amount of liquid to be disposed within the housing prior to delivery, the number and size of the exhaust ports, and the operating frequency at which the device operates. It is also contemplated that the lower housing member 427 may be configured similar to the nozzle 27 of the embodiment of FIGS. 1-10 with one or more exhaust ports 83 formed in a tip 81 of the nozzle.

The liquid inlet 457 extends transversely through the sidewall 552 of the lower housing member 427 into fluid communication with the internal chamber 455 of the housing 423. It is contemplated, however, that the liquid inlet 457 may be disposed substantially anywhere along the side of the lower housing member 427, or along the side of the upper housing member 425, or even extend axially through the top of the upper housing member and remain within the scope of this invention. Thus, the internal chamber 455 illustrated in FIG. 11 broadly defines a liquid flow path along which liquid flows within the housing 423 to the exhaust port 483 for exhausting the liquid from the housing.

The device 423 illustrated in FIG. 11 lacks a valve member (e.g., a valve member similar to the valve needle 53 of the embodiment of FIGS. 1-10) or other component disposed within the housing to the control the flow of liquid to the exhaust port 483. Rather, in this second embodiment the liquid may flow continuously within the internal chamber 455 to the exhaust port 483. It is understood, however, that a suitable control system (not shown) external of the housing 423 may control the flow of liquid to the housing inlet 457 to thereby control the delivery of liquid to the exhaust port 483 without departing from the scope of this invention.

An elongate ultrasonic waveguide assembly, generally indicated at 550, extends axially of the housing 423 (e.g., in the longitudinal or vertical direction of the housing illustrated in FIG. 11) and is disposed entirely within the internal chamber 455 of the housing. In particular, the waveguide assembly 550 may suitably be constructed in substantially the same manner as the waveguide assembly 150 of the fuel injector 21 of the embodiment of FIGS. 1-10. The terminal end 523 of the waveguide 521 of the assembly 550 is suitably disposed proximate to the exhaust port 483. The term "proximate" is used here in a qualitative sense only to mean that ultrasonic energy is imparted by the terminal end 523 of the waveguide 521 to liquid in the internal chamber 455 just prior to the liquid entering the exhaust port 483, and is not intended to refer to a specific spacing between the exhaust port and the terminal end of the waveguide.

As illustrated in FIG. 11, the inner cross-sectional dimension of the sidewall 552 of the lower housing member 427 decreases toward the lower end 481 of the lower housing member. The enlarged portion 695 at and/or adjacent to the terminal end 523 of the waveguide 521 is thus in closely spaced or even sliding contact relationship with the sidewall 552 toward the lower end 481 of the lower housing member 427, e.g., just upstream (relative to the direction in which pressurized liquid flows within the internal chamber 455 to the exhaust port 483) of the exhaust port so that the flow path of the liquid within the housing narrows at and/or adjacent the terminal end of the waveguide.

It is understood, however, that the terminal end 523 of the waveguide 521 (or other segment thereof) need not be in closely spaced relationship with the sidewall 552 of the lower housing member 427 to remain within the scope of this invention. For example, the outer cross-sectional dimension of the waveguide 521 may be substantially uniform along its length instead of having the enlarged portion 695, or it may narrow toward the terminal end 523 of the waveguide. Alternatively, or additionally, the inner cross-sectional dimension of the sidewall 552 of the lower housing member 427 may not decrease toward the lower end 481 of the lower housing member.

The waveguide 521 is suitably interconnected to the housing 423 within the internal chamber 455 by a transversely extending mounting member 479 constructed substantially similar to the mounting member 79 of the embodiment of FIGS. 1-10. Accordingly, the mounting member 479 vibrationally isolates the housing 423 from mechanical vibration of the waveguide 521. The outer segment 689 of the mounting member 479 is secured between the lower end 431 of the upper housing member 425 and the upper end 433 of the lower housing member 427. Suitable ports (not shown but similar to the ports 199, 201 illustrated in the embodiment of FIGS. 1-10) may be formed in the upper and lower housing members 425, 427 where the outer segment 689 of the mounting member 479 is secured therebetween to permit liquid to flow longitudinally within the internal chamber past the mounting member.

The waveguide assembly 550 also comprises the excitation device 545 (e.g., the piezoelectric rings 547 in the illustrated embodiment), which is compressed against the mounting member 479 by the collar 551 threadably fastened to the upper segment 531 of the waveguide 521. Electrical current is supplied to the excitation device 545 by suitably wiring (not shown but similar to the wiring 181, 183 of the embodiment of FIGS. 1-10) extending through the side of the housing 423 and electrically connected to the contact ring 683 within the internal chamber 455.

In operation, liquid is delivered to the liquid inlet 457 of the housing 423 for flow along the flow path, e.g., within the internal chamber 455, to the exhaust port 483. As pressurized liquid flows past the terminal end 523 of the waveguide 521 to the exhaust port 483, the waveguide assembly 450 is operated in substantially the same manner as the waveguide assembly 150 of the fuel injector 21 of FIGS. 1-10 to ultrasonically vibrate the terminal end of the waveguide, such as in the manner of an ultrasonic horn. Ultrasonic energy is thus imparted by the terminal end 523 of the waveguide 521 to the liquid just prior to the liquid entering the exhaust port 483 to generally atomize the liquid (e.g., to decrease droplet size and narrow the droplet size distribution of the liquid exiting the device 421). Ultrasonic energization of the liquid before it exits the exhaust port 483 generally produces a pulsating, generally cone-shaped spray of atomized liquid delivered from the device 421.

Figure 12:
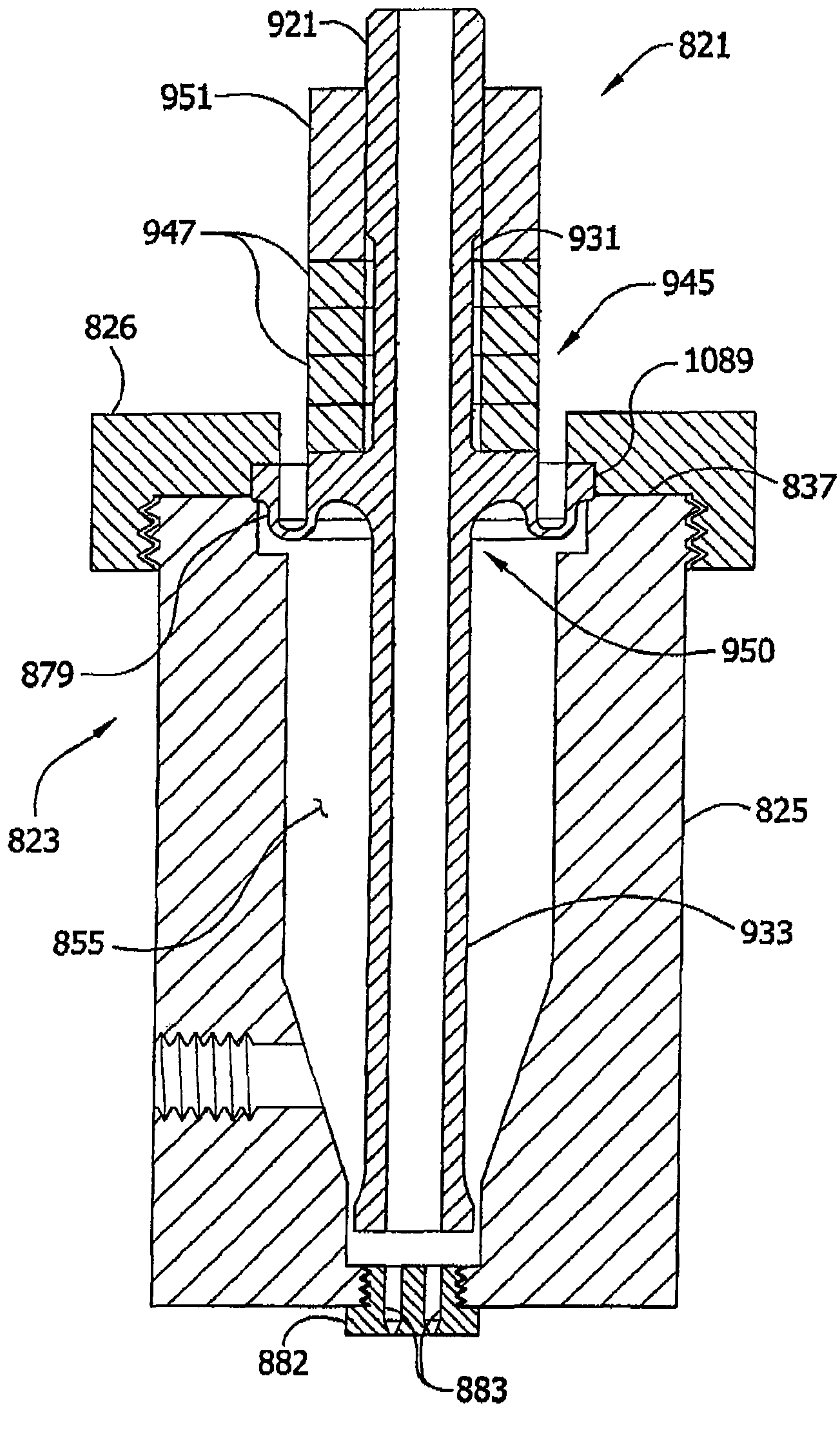
FIG. 12 is a longitudinal cross-section of an ultrasonic liquid delivery device according to a third embodiment of the present invention.

FIG. 12 illustrates an ultrasonic liquid delivery device, generally indicated at 821, according to a third embodiment of the present invention. The device 821 of this third embodiment is similar to that of the second embodiment except that the waveguide assembly 950 of the this third embodiment is illustrated as being only partially disposed within the internal chamber 855 of the housing 823. The housing 823 of this third embodiment comprises a housing member 825 defining the internal chamber 855, and a closure 826 (e.g., an annular closure in the illustrated embodiment) threadably fastened over an open upper end 837 of the housing member to further define the housing and to secure the outer segment 1089 of the mounting member 879 between the closure and the housing member to thereby secure the mounting member (and hence the waveguide assembly 850) in place. The mounting member 879 thus vibrationally isolates the housing 823 from mechanical vibration of the waveguide 921 as described previously in connection with the first and second embodiments. The insert 882 of this third embodiment is illustrated as having a plurality of exhaust ports 883.

In the embodiment illustrated in FIG. 12, the lower segment 933 of the waveguide 921 extends entirely within the internal chamber 855 while the upper segment 931 of the waveguide extends up from the mounting member 879 axially outward of the housing 823. The excitation device 945, e.g., the piezoelectric rings 947, are accordingly disposed exterior of the housing 823 along with the collar 951 that compresses the rings against the upper surface of the mounting member 879. Electrical current may be delivered to the excitation device 945 by suitable wiring (not shown) without the need for the sleeve 155, contact ring 165 and guide ring 167 associated with the fuel injector 21 illustrated in FIGS. 1-10. However, it is understood that such a sleeve, contact ring and guide ring may be incorporated into the device 821 illustrated in FIG. 12 without departing from the scope of this invention.

Figure 13:
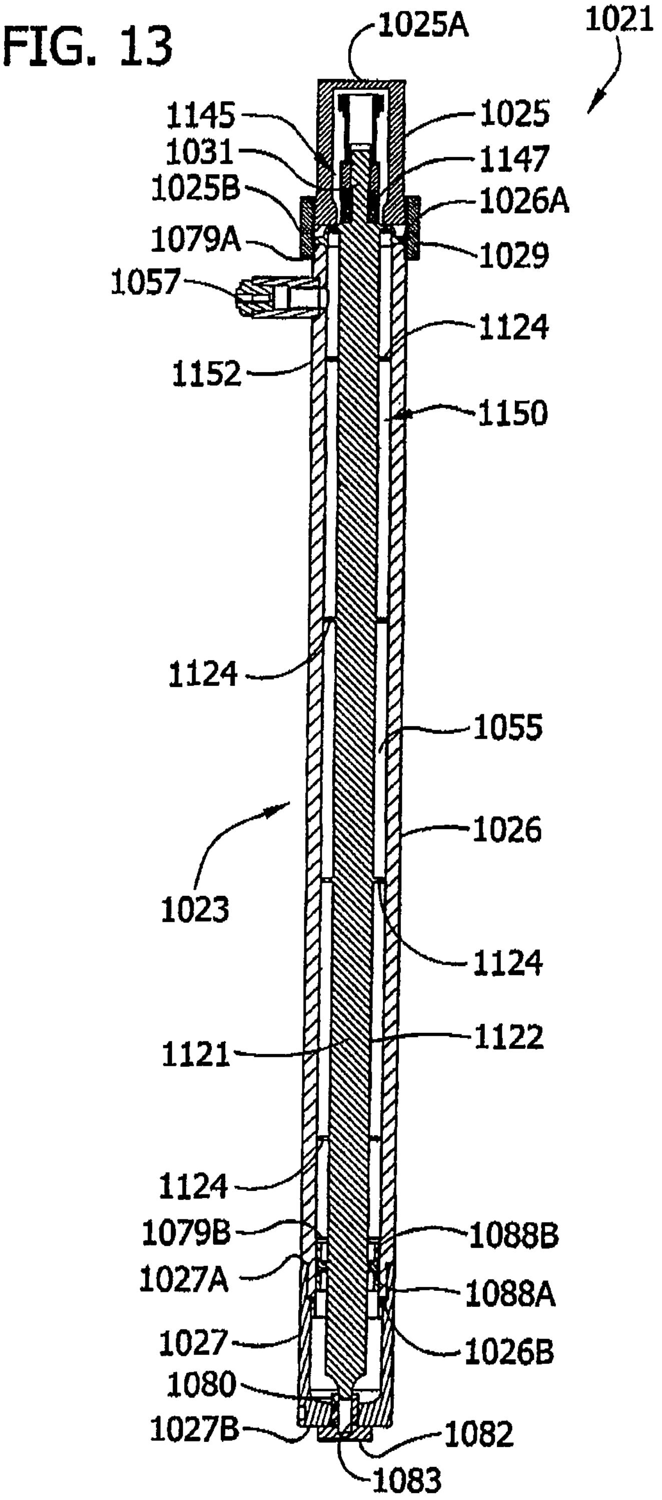
FIG. 13 is a longitudinal cross-section of an ultrasonic liquid delivery device according to a fourth embodiment of the present invention.

FIG. 13 illustrates a fourth embodiment of an ultrasonic liquid delivery device, generally indicated at 1021. The device 1021 of this fourth embodiment is broadly described herein with reference to any ultrasonically driven device in which a pressurized spray of liquid is exhausted from the device following application of ultrasonic energy to the liquid, it being contemplated that such a device may have application in apparatus such as, without limitation, nebulizers and other drug delivery devices, molding equipment, humidifiers, fuel injection apparatus for engines, paint spray systems, ink delivery systems, mixing systems, homogenization systems, spray drying systems, cooling systems and other applications in which an ultrasonically generated spray of liquid is utilized.

The illustrated device 1021 comprises an elongate housing, designated generally at 1023, having an upper housing member 1025 (with respect to the vertical orientation of the device illustrated in FIG. 13), an intermediate housing member 1026, and a lower housing member 1027. The upper housing member 1025 includes a closed upper end 1025A and an open lower end 1025B. The intermediate housing member 1026 is open at its longitudinal ends 1026A, 1026B. The lower housing member 1027 includes an open upper end 1027A and a lower end 1027B. The lower end 1025B of the upper housing member 1025 seats against the upper end 1026A of the intermediate housing member 1026 and the housing members are secured together by a suitable threaded connector 1029. The lower end 1026B of the intermediate housing member 1026 connects (e.g., a threaded connection, snap-fit, or other suitable connection) to the upper end 1027A of the lower housing member 1027. As a result, the upper, intermediate, and lower housing members 1025, 1026, 1027 together define an internal chamber 1055 of the housing 1023. It is contemplated that the housing may alternatively be constructed of less than three pieces, or more than three pieces, within the scope of this invention.

In the embodiment of the device 1021 illustrated in FIG. 13, the intermediate housing member 1026 has a length that is significantly greater than the lengths of the upper and lower housing members 1025, 1027. It is understood, however, that the relative lengths of each of these housing members can vary. For example, the upper, intermediate, and lower housing members 1025, 1026, 1027 can be equal in length, the upper member can have a length greater than the intermediate and lower housing members, or the lower housing member can have a length greater than the upper and intermediate housing members.

An opening 1057 in a sidewall 1152 of the intermediate housing member 1026 adjacent its upper end 1026A defines an inlet 1057 for receiving liquid into the internal chamber 1055 of the housing 1023. It is contemplated, however, that the inlet 1057 may be disposed substantially anywhere along the side of the lower housing member 1027, along the side of the intermediate housing member 1026, or along the side of the upper housing member 1025, or extend through the closed end 1025A of the upper housing member and remain within the scope of this invention.

The lower end 1027B of the lower housing member 1027 has an axially extending threaded bore 1080 for threadably receiving an insert 1082 therein such that the insert further defines the housing 1023 of the device 1021. An exhaust port 1083 extends axially through the insert 1082 to broadly define an exhaust port (or outlet) of the housing 1023 through which liquid is exhausted from the housing. While the insert 1082 illustrated in FIG. 13 has a single exhaust port 1083, it is contemplated that the insert may comprise more than one exhaust port. It is also contemplated that the insert 1082 may be omitted altogether and the lower end 1027B of the lower housing member 1027 may be formed with one or more exhaust ports 1083 therein.

The internal chamber 1055 of the housing 1023 broadly defines a liquid flow path along which liquid can flow within the housing 1023 from the inlet 1057 to the exhaust port 1083 for exhausting the liquid from the internal chamber of the housing. While the device 1021 illustrated in FIG. 13 has a single inlet 1057 and a single exhaust port 1083, it is contemplated that the device may comprise more than one inlet and/or more than one exhaust port. The housing 1023 of the illustrated embodiment is generally cylindrical but may suitably be of any shape, and may be sized depending at least in part on the desired amount of liquid to be disposed within the housing prior to delivery, the number and size of the inlets and exhaust ports, and the operating frequency at which the device operates.

An elongate ultrasonic waveguide assembly, generally indicated at 1150, extends axially of the housing 1123 (e.g., in the longitudinal or vertical direction of the housing illustrated in FIG. 13). The ultrasonic waveguide assembly comprises an ultrasonic waveguide 1121 and an excitation device 1145 held in assembly in the manner described previously in connection with the embodiment of FIGS. 1-10. As illustrated in FIG. 13, at least a portion of the waveguide 1121 is disposed within the internal chamber 1055 of the housing 1023 and, more specifically, in the liquid flow path from the inlet to the exhaust port so that liquid flowing from the inlet 1057 to the exhaust port 1083 is in direct fluid contact with the waveguide.

In one suitable embodiment, the entire ultrasonic waveguide assembly 1150 is disposed within the internal chamber 1055 of the housing 1023. In one arrangement, as illustrated in FIG. 13, the excitation device 1145 is disposed within the internal chamber 1055 but is isolated from the liquid flow path. As a result, liquid passing through the internal chamber 1055 of the housing 1023 does not contact the excitation device 1145. It is understood, however, that the excitation device 1145 can be within the liquid flow path, e.g., if the inlet 1057 is located in the upper end 1025A of the upper housing member 1025.

The ultrasonic waveguide 1121 of this embodiment comprises an elongate, generally cylindrical body having an outer surface 1122. The ultrasonic waveguide 1121 suitably includes a plurality of axially aligned one-half wavelength segments so that the waveguide has one or more nodal regions and two or more antinodal regions. The illustrated waveguide 1121, for example, has five one-half wavelength segments defining five nodal regions and six antinodal regions. It is contemplated, however, that the ultrasonic waveguide 1121 may have more or fewer one-half wavelength segments than five including a single one-half wavelength segment. A single one-half wavelength segment would have one nodal region and two antinodal regions. In one embodiment, the one-half wavelength segments are formed separate from each other and connected end-to-end (e.g., by threaded connection or other suitable connection) to form the waveguide. It is understood, though, that the waveguide may be of single piece construction without departing from the scope of this invention.

As used herein, the "antinodal region" of the ultrasonic waveguide 1121 refers to a longitudinal region or segment of the ultrasonic waveguide along which little (or no) transverse displacement occurs during ultrasonic vibration of the ultrasonic waveguide and longitudinal (e.g., axial in the illustrated embodiment) displacement of the ultrasonic waveguide is generally maximized. In the illustrated embodiment, the ultrasonic waveguide 1121 is such that the antinodal region is particularly defined by an antinodal plane (i.e., a plane transverse to the ultrasonic waveguide at which no transverse displacement occurs while longitudinal displacement is generally maximized) is present. This plane is also sometimes referred to as an antinodal point.

The excitation device 1145 (e.g., the piezoelectric rings 1147 in the illustrated embodiment), is in direct contact with an upper segment 1031 of the ultrasonic waveguide 1121. Electrical current is supplied to the excitation device 1145 by suitable wiring (not shown but similar to the wiring 181, 183 of the embodiment of FIGS. 1-10) extending through the side of the housing 1023 and electrically connected to a contact ring (similar to the contact ring 165 of the embodiment of FIGS. 1-10) within the internal chamber 1055.

As illustrated in FIG. 13, at least one agitating member 1124 extends at least in part transversely outward from the outer surface 1122 of the ultrasonic waveguide 1121. In the illustrated embodiment, a plurality of agitating members 1124 is illustrated in the form of four washer-shaped rings that extend continuously about the circumference of the ultrasonic waveguide 1121 in longitudinally spaced relationship with each other and transversely (e.g., radially in the illustrated embodiment) outward from the outer surface 1122 of the ultrasonic waveguide. In this manner, the vibrational displacement of each of the rings relative to the ultrasonic waveguide 1121 is relatively uniform about the circumference of the ultrasonic waveguide. Each of the agitating members 1124 is disposed in the internal chamber 1055 of the housing 1023 and specifically within the liquid flow path between the inlet 1057 and the exhaust port 1083. As a result, liquid flowing through the flow path from the inlet 1057 to the exhaust port 1083 passes each of the agitating members 1124.

It is understood, however, that the agitating members 1124 need not each be continuous about the circumference of the ultrasonic waveguide 1122. For example, the agitating members 1124 may instead be in the form of spokes, blades, fins or other discrete structural members that extend transversely outward from the outer surface 1122 of the ultrasonic waveguide 1122. It is understood that the number of agitating members 1124 (e.g., the rings in the illustrated embodiment) may be less than or more than four without departing from the scope of this invention. It is also understood that the longitudinal spacing between the agitating members 1124 may be other than as illustrated in FIG. 13 (e.g., either closer or spaced further apart). While the agitating members 1124 illustrated in FIG. 13 are equally longitudinally spaced from each other, it is contemplated that where more than two agitating members are present the spacing between longitudinally consecutive agitating members need not be uniform to remain within the scope of this invention.

The locations of the agitating members 1124 on the ultrasonic waveguide 1121 are at least in part a function of the intended vibratory displacement of the agitating members upon vibration of the ultrasonic waveguide. In one suitable embodiment, each of the agitating members 1124 is positioned at a respective antinodal region of the ultrasonic waveguide 1121 to maximize longitudinal movement of the agitating members along the flow path while minimizing their transverse movement. It is understood that the agitating members 1124 can be spaced from the antinodal region of the ultrasonic waveguide 1121 without departing from the scope of this invention. It is further understood that for embodiments that include two or more agitating members 1124, agitating members 1124 may be located at both an antinodal region and a nodal region of the ultrasonic waveguide.

The agitating members 1124 are sufficiently constructed (e.g., in material and/or dimension such as thickness and transverse length, which is the distance that the agitating member extends transversely outward from the outer surface 1122 of the ultrasonic waveguide 1121) to facilitate dynamic motion, and in particular dynamic flexing/bending of the agitating members 1124 in response to the ultrasonic vibration of the ultrasonic waveguide. While the agitating members 1124 (e.g., the rings) illustrated in FIG. 13 are relatively flat, i.e., relatively rectangular in cross-section, it is understood that the rings may have a cross-section that is other than rectangular without departing from the scope of this invention. The term cross-section is used in this instance to refer to a cross-section taken along one transverse direction (e.g., radially in the illustrated embodiment) relative to the outer surface 1122 of the ultrasonic waveguide 1121). Additionally, although the agitating members 1124 (e.g., the rings) illustrated in FIG. 13 are constructed only to have a transverse component, it is contemplated that one or more of the agitating members may have at least one longitudinal (e.g., axial) component to take advantage of transverse vibrational displacement of the ultrasonic waveguide 1121 (e.g., at and near the nodal region of the ultrasonic waveguide illustrated in FIG. 13) during ultrasonic vibration of the ultrasonic waveguide assembly 1150. For example, one or more of the agitating members 1124 can be formed with a generally T-shaped cross-section, a L-shaped cross-section, a plus-shaped cross-section, or other suitable cross-section.

The waveguide assembly 1150 is suitably interconnected to the housing 1023 within the internal chamber 1055 by a transversely extending mounting member 1079A (broadly, “a first isolating member”) constructed substantially similar to the mounting member 79 of the embodiment of FIGS. 1-10. The mounting member vibrationally isolates the housing 1023 from mechanical vibration of the waveguide 1121. It is understood that more than one mounting member can be provided. As illustrated in FIG. 13, the mounting member 1079A is formed as one-piece with the waveguide assembly 1150 but it is contemplated that the mounting member can be formed as a separate piece.

In the illustrated embodiment, the mounting member 1079A is affixed to the housing 1023 at the junction of the upper and intermediate housing members 1025, 1026, which is aligned with one of the nodal region of the ultrasonic waveguide 1121. As a result, the mounting member 1079 inhibits transverse movement of the waveguide assembly 1150. It is contemplated that the mounting member 1079A can have different locations along the length of the ultrasonic waveguide 1121 including in the antinodal region without departing from the scope of this invention.

The waveguide assembly 1150 is axially supported within the internal chamber 1055 of the housing 1023 by a stabilizing member 1079B (broadly, “a second isolating member”) spaced longitudinally from the mounting member. The stabilizing member 1079B includes a radial component 1088A and an axial component 1088B as described in U.S. Pat. No. 6,676,003, the disclosure of which is incorporated herein by reference to the extent it is consistent herewith. The stabilizing member 1079B cooperates with the mounting member 1079A to vibrationally isolate the housing 1023 from mechanical vibration of the waveguide 1121.

In one suitable embodiment, the stabilizing member 1079B is positioned in the nodal region of the ultrasonic waveguide 1121 to inhibit transverse movement of the waveguide assembly 1150. It is contemplated that the stabilizing member 1079B can have different locations along the length of the ultrasonic waveguide 1121 including in the antinodal region without departing from the scope of this invention. As illustrated in FIG. 13, the stabilizing member 1079B is disposed within the internal chamber 1055 of the housing 1023 intermediate the inlet 1057 and the exhaust port 1083 such that the stabilizing member is disposed within the flow path. As a result, the stabilizing member 1079B includes openings (not shown) for allowing liquid to pass the stabilizing member as it flows from the inlet 1057 to the exhaust port 1083.

The stabilizing member 1079B is sized and shaped relative to the housing 1023 so that it has a friction fit with the housing. More specifically, the radial component 1088A of the stabilizing member 1079B contacts the inner surface of the housing 1023 with sufficient frictional resistance that during dynamic displacement of the ultrasonic waveguide 1121, the radial component 1088A remains stationary with respect to the housing. The axial component 1088B of the stabilizing member 1079B bends/flexes during dynamic displacement of the ultrasonic waveguide 1121 so that the ultrasonic waveguide can move without movement of the radial component 1088A. The stabilizing member 1079B, however, is capable of sliding movement relative to the housing 1023 in the axial (longitudinal) direction so that the ultrasonic waveguide can be inserted into and removed from the internal chamber 1055 of the housing 1023. It is understood that more than one stabilizing members can be provided. As illustrated in FIG. 13, the stabilizing member 1079B is formed as one-piece with the waveguide assembly 1150 but it is contemplated that the stabilizing member can be formed as a separate piece.

In operation, liquid is delivered to the liquid inlet 1057 of the housing 1023 for flow along the flow path, e.g., within the internal chamber 1055, to the exhaust port 1083. As pressurized liquid flows along the waveguide 1121 toward the exhaust port 1083, the waveguide assembly 1050 is operated in substantially the same manner as the waveguide assembly 150 of the fuel injector 21 of FIGS. 1-10 to ultrasonically vibrate the waveguide. Ultrasonic energy is thus imparted by ultrasonic waveguide 1121 to the liquid prior to the liquid exiting the flow path via exhaust port 1083 to generally atomize the liquid (e.g., to decrease droplet size and narrow the droplet size distribution of the liquid exiting the device 1021). Ultrasonic energization of the liquid before it exits the exhaust port 1083 generally produces a pulsating, generally cone-shaped spray of atomized liquid delivered from the device 1021. Moreover, the agitating members 1124 mix the liquid as it flows through the flow path. Certain liquids (e.g., solutions) can unwantingly separate into various phases. The agitating members 1124 agitate the liquid during operation of the ultrasonic waveguide 1121 as the liquid passes the agitating members to thereby maintain the liquid in a mixed state. More specifically, the agitating members 1124 are dynamically displaced longitudinally relative to the housing 1023 within the liquid flow path due to their placement within the antinodal region of the ultrasonic waveguide 1121.

Figure 14:
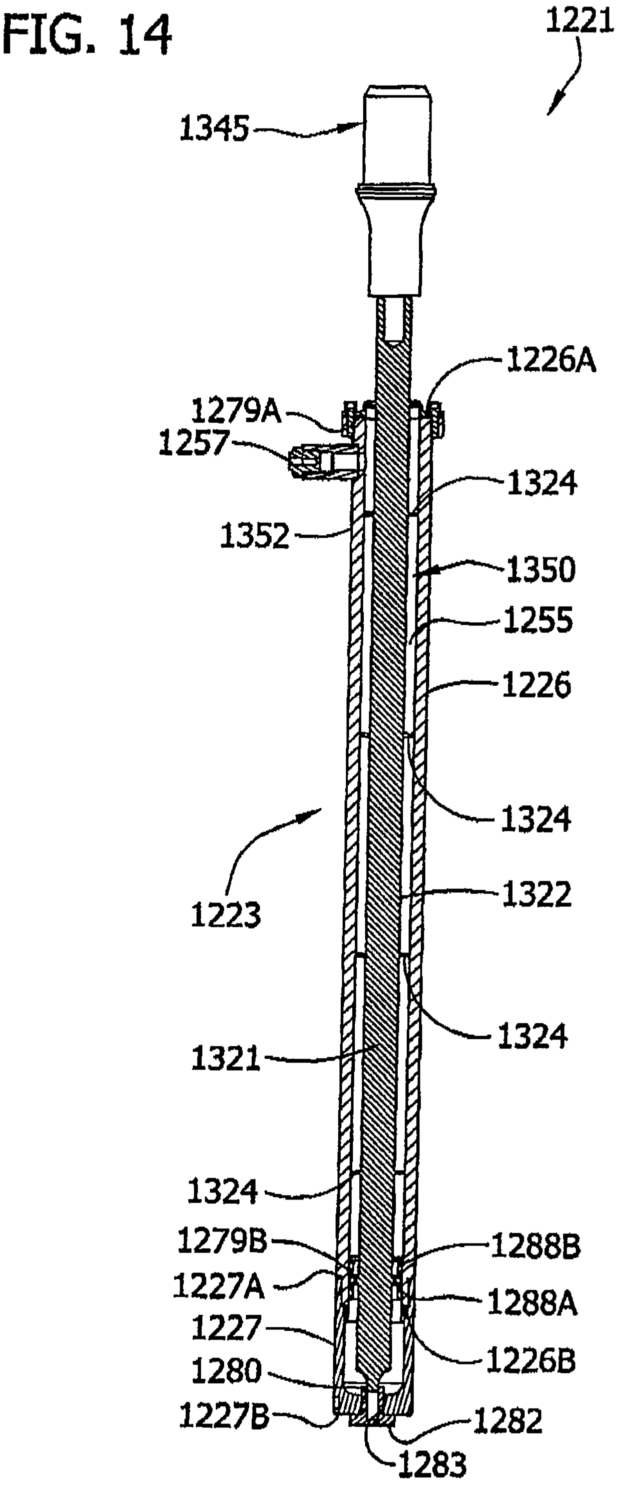
FIG. 14 is a longitudinal cross-section of an ultrasonic liquid delivery device according to a fifth embodiment of the present invention.

FIG. 14 illustrates an ultrasonic liquid delivery device, generally indicated at 1221, according to a fifth embodiment of the present invention. The device 1221 of this fifth embodiment is similar to that of the fourth embodiment except that a waveguide assembly 1350 of this fifth embodiment is illustrated as being only partially disposed within an internal chamber 1255 of a housing 1223. The housing 1223 of this fifth embodiment comprises an internal chamber 1255, and a closure (e.g., a first mounting member 1279A in the illustrated embodiment) closing an open, upper end 1226A of an upper housing member 1226 to further define the internal chamber. In the embodiment illustrated of FIG. 14, a lower segment of the ultrasonic waveguide 1321 extends entirely within the internal chamber 1255 while an upper segment of the ultrasonic waveguide extends up from the first mounting member 1279A axially outward of the housing 1223. An excitation device 1345 is accordingly disposed exterior of the housing 1223. Electrical current may be delivered to the excitation device 1345 by suitable wiring (not shown) without the need for the sleeve, contact ring and guide ring associated with the fuel injector 21 illustrated in FIGS. 1-10. However, it is understood that such a sleeve, contact ring and guide ring may be incorporated into the device 1221 illustrated in FIG. 14 without departing from the scope of this invention. The embodiment illustrated in FIG. 14 is well suited for uses having liquid that is too hot for the excitation device 1345. Not only does this embodiment isolate the excitation device 1345 from the liquid passing through the internal chamber 1255 of the housing 1223 but also allows for cooling air to be supplied to the excitation device to maintain the excitation device within an acceptable range.

Each of the embodiments set forth in FIGS. 13 and 14 also broadly defines respective embodiments of an ultrasonic liquid treatment and delivery system in which a liquid is ultrasonically treated such as to agitate or mix the liquid and then further ultrasonically energized just prior to exiting the system to generate a spray of the liquid from the system. For example, with reference to the embodiment of FIG. 12, the ultrasonic waveguide 1121 broadly includes a first ultrasonic waveguide (e.g., that portion of the waveguide 1121 that includes the agitating members 1124) and a second ultrasonic waveguide (e.g., that portion of the waveguide 1121 extending below the lowermost agitating member 1124 to the terminal end of the waveguide) connected end-to-end to each other.

In accordance with one process for ultrasonically treating and delivering a liquid (e.g., fuel) from such a system (e.g., where the liquid is fuel, for delivering the fuel to an internal combustion engine in the form of a spray of fuel droplets), liquid flows along the flow path of the system from the inlet 1057 of the housing 1023 to the exit, or exhaust port 1083. The liquid is thus directed to flow along the flow path over the first ultrasonic waveguide (i.e., the portion of the waveguide 1121 that includes at least one and in the illustrated embodiment the plurality of agitating members 1124). The excitation device 1145 excites the first ultrasonic waveguide and agitating members 1124 to agitate or mix the liquid as it flows along the flow path. For example, where the liquid is fuel, the fuel is agitated by the agitating members to inhibit phase separation (and/or to facilitate homogenization) of the fuel components.

The liquid is further directed along the flow path to flow over the second ultrasonic waveguide (i.e., the portion of the waveguide 1121 from the lowermost agitating member 1124 to the terminal end of the waveguide) toward the exhaust port 1083. The second ultrasonic waveguide is ultrasonically excited, e.g., by the excitation device 1145, to ultrasonically energize the liquid just prior to the liquid exiting the system (e.g., to atomize or reduce the droplet size and narrow the droplet distribution of the liquid) through the exhaust port 1083 for further processing (e.g., where the liquid is fuel, for delivery to an engine in the form a spray of droplets).

Figure 15:
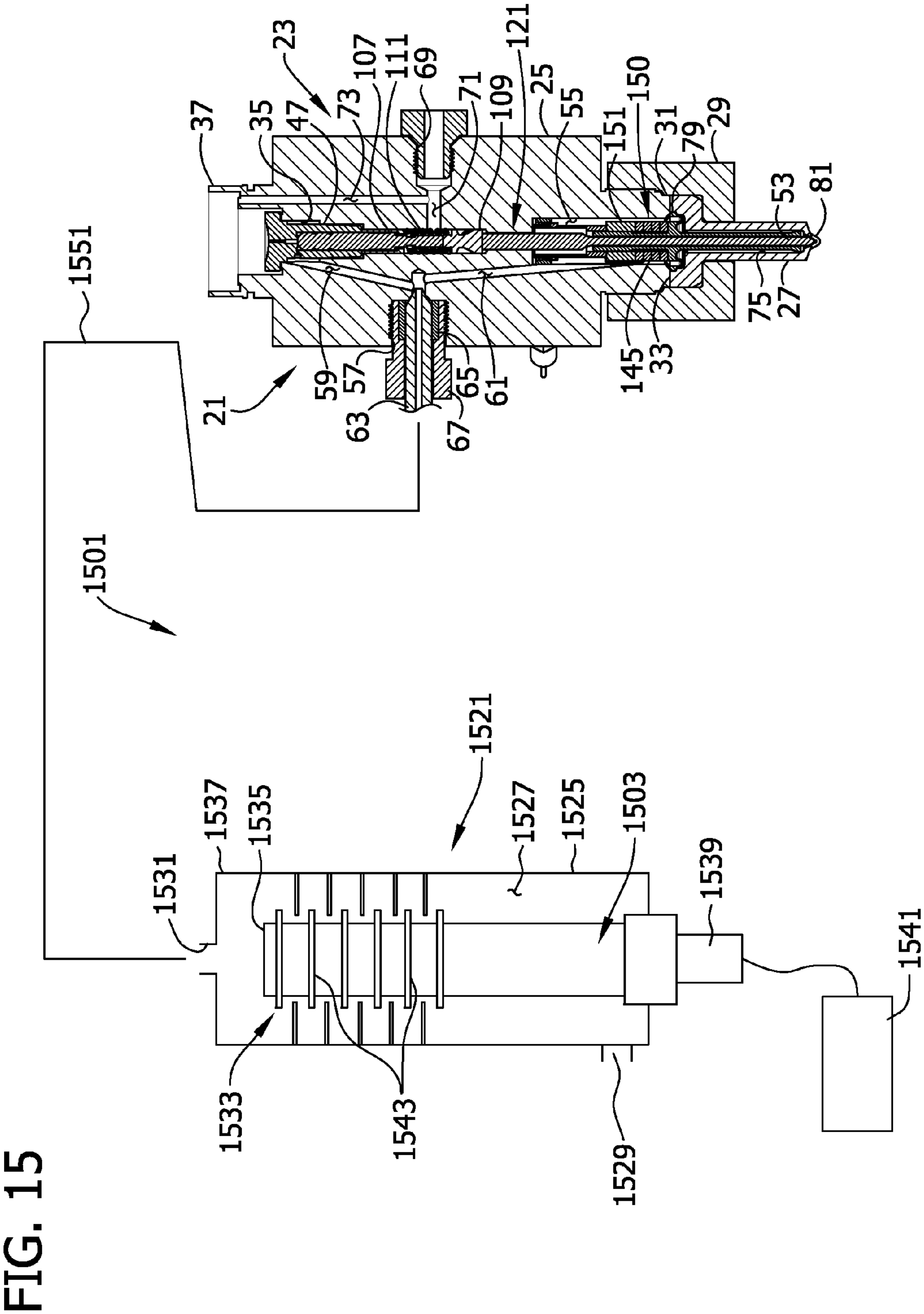
FIG. 15 is a schematic of one embodiment of an ultrasonic liquid treatment and delivery device.

FIG. 15 illustrates another embodiment of an ultrasonic liquid treatment and delivery system, generally indicated at 1501, in which first and second ultrasonic waveguides 1503 and 121, respectively, are separate from each other. In particular, the system 1501 of FIG. 15 comprises an ultrasonic treatment device, generally indicated at 1521, and a separate ultrasonic delivery device, generally indicated at 21. The ultrasonic treatment device 1521 is substantially similar to that described in co-assigned U.S. patent application Ser. No. 11/530,311 filed Sep. 8, 2006, the entire disclosure of which is incorporated herein by reference.

In particular, the treatment device 1521 comprises a housing 1525 having an internal chamber 1527, an inlet 1529 in fluid communication with the internal chamber for receiving one or more liquids and other components into the chamber, and an outlet 1531 in fluid communication with the internal chamber and through which liquid exits the housing. An ultrasonic waveguide assembly, generally indicated at 1533, extends longitudinally at least in part within the internal chamber 1527 to ultrasonically energize liquid (and any other components) flowing through the internal chamber. In particular, the ultrasonic waveguide assembly 1533 of the illustrated embodiment extends longitudinally from the lower or inlet 1529 end of the chamber 1527 up toward the outlet 1531 end of the chamber to a terminal end 1535 of the waveguide assembly. More suitably, the waveguide assembly 1533 is mounted, either directly or indirectly, to the housing 1525.

The ultrasonic waveguide assembly 1535 suitably comprises an ultrasonic waveguide 1503 (e.g., an ultrasonic horn, broadly defining the first ultrasonic waveguide) disposed entirely with the internal chamber 1527 of the housing 1525 for complete submersion within the liquid being treated within the chamber, and more suitably it is aligned coaxially with a chamber sidewall 1537. The ultrasonic waveguide 1503 has an outer surface that together with the inner surface of the sidewall 1537 defines a flow path within the internal chamber 1527 along which liquid and other components flow past the waveguide within the chamber. The waveguide assembly 1535 of the illustrated embodiment also comprises a booster 1539 coaxially aligned with and connected at an upper end thereof to a lower end of the waveguide 1503. It is understood, however, that the waveguide assembly 1535 may comprise only the waveguide 1503 and remain within the scope of this invention. It is also contemplated that the booster 1539 may be disposed entirely exterior of the housing 1525, with the waveguide 1503 mounted on the housing, without departing from the scope of this invention.

The ultrasonic waveguide assembly 1535, and more particularly the booster 1539 in the illustrated embodiment of FIG. 15, is suitably mounted on the housing 1527 by a mounting member (not shown) that is configured to vibrationally isolate the waveguide assembly (which vibrates ultrasonically during operation thereof) from the ultrasonic treatment device housing 1525. That is, the mounting member inhibits the transfer of longitudinal and transverse mechanical vibration of the waveguide assembly 1535 to the housing 1525 while maintaining the desired transverse position of the waveguide assembly (and in particular the waveguide 1503)

within the internal chamber 1527 and allowing both longitudinal and transverse displacement of the waveguide within the housing.

A suitable ultrasonic drive system 1541 (shown schematically in FIG. 15 and broadly defining an excitation device) including at least an exciter (not shown) and a power source (not shown) is disposed exterior of the housing 1525 and operatively connected to the booster 1539 (and more broadly to the waveguide assembly 1535) to energize the waveguide assembly to mechanically vibrate ultrasonically. Examples of suitable ultrasonic drive systems 1541 include a Model 20A3000 system available from Dukane Ultrasonics of St. Charles, Ill., and a Model 2000CS system available from Herrmann Ultrasonics of Schaumberg, Ill. In one embodiment, the drive system 1539 is capable of operating the waveguide assembly 1535 at a frequency in the range of about 15 kHz to about 100 kHz, more suitably in the range of about 15 kHz to about 60 kHz, and even more suitably in the range of about 20 kHz to about 40 kHz. Such ultrasonic drive systems 1539 are well known to those skilled in the art and need not be further described herein.

At least one and more suitably a plurality of agitating members 1543 are connected to the ultrasonic waveguide 1503 and extend at least in part transversely outward from the outer surface of the waveguide in longitudinally spaced relationship with each other. The size, construction, configuration, arrangement and operation of the one or more agitating members 1543 is suitably in accordance with the agitating members 1124, 1324 described previously and illustrated in FIGS. 13 and 14 and in the previously filed U.S. patent application Ser. No. 11/530,311.

The ultrasonic delivery device 21 illustrated in FIG. 15 is substantially similar to the delivery device of FIG. 1 including a housing 23 having an internal chamber 55, an inlet 57, an outlet or exhaust port (not shown in FIG. 15 but identical to the exhaust port 83 of FIG. 7), an ultrasonic waveguide 121 (broadly, the second ultrasonic waveguide), a valve member 53 and an excitation device 145. The inlet 57 to the ultrasonic delivery device housing 23 is in fluid or flow communication with the outlet 1531 of the treatment device housing 1525, such as by a suitable conduit 1551, so that liquid exiting the treatment device flows into the internal chamber 55 of the ultrasonic delivery device via the inlet of the delivery device housing.

In another suitable embodiment, the ultrasonic delivery device may instead be a continuous flow device such as that illustrated in either of the embodiments of FIGS. 11 and 12.

In operation according to a process for ultrasonically treating and delivering a liquid, such as fuel, the liquid is directed to flow into the housing 1525 of the ultrasonic treatment device 1521 and to further flow along the flow path therein over the waveguide 1503 and agitating members 1543. The drive system 1541 ultrasonically excites the waveguide 1503 and agitating members 1543 to thereby agitate or mix the liquid. The liquid then flows out of the treatment device 1521 via the outlet 1531 thereof and flows along a flow path through the conduit 1551 to the inlet 57 of the ultrasonic delivery device 21. The liquid then flows along the flow path within the delivery device housing 23 over the terminal end of the ultrasonic waveguide 121 within the housing.

The excitation device 145 operates to ultrasonically excite the waveguide 121 within the delivery device housing 23 to ultrasonically energize the liquid just prior to the liquid exiting the delivery device housing. For example, where the liquid is fuel, the fuel is energized as it flows over the terminal end of the waveguide 121 and to the exhaust port to generally atomize the fuel (e.g., to decrease droplet size and narrow the droplet size distribution of the fuel exiting the device). In the embodiment illustrated in FIG. 15 where the device 21 includes the valve member 53, the excitation device 145 is suitably operable in the open position of the valve member to ultrasonically excite the delivery device waveguide 121.

It is contemplated that a liquid other than fuel may be treated and delivered using the above described system without departing from the scope of this invention. For example, without limitation, molten bitumens, viscous paints, hot melt adhesives, thermoplastic materials that soften to a flowable form when exposed to heat and return to a relatively set or hardened condition upon cooling (e.g., crude rubber, wax, polyolefins and the like), syrups, heavy oils, inks, liquid medication, emulsions, slurries, suspensions and combinations thereof may be treated and delivered by the above described system.

When introducing elements of the present invention or preferred embodiments thereof, the articles “a”, “an”, “the”, and “said” are intended to mean that there are one or more of the elements. The terms “comprising”, “including”, and “having” are intended to be inclusive and mean that there may be additional elements other than the listed elements.

As various changes could be made in the above constructions and methods without departing from the scope of the invention, it is intended that all matter contained in the above description and shown in the accompanying drawings shall be interpreted as illustrative and not in a limiting sense.

What is claimed is:

1. An ultrasonic liquid treatment and delivery system comprising:

an ultrasonic treatment device comprising:

a housing having an internal chamber and an inlet in fluid communication with the internal chamber of the housing whereby liquid enters the internal chamber and an outlet in fluid communication with the internal chamber of the housing through which liquid exits the ultrasonic treatment device;

an ultrasonic waveguide disposed at least in part within the internal chamber of the housing to ultrasonically energize liquid within the internal chamber prior to said liquid being exhausted from the housing through the outlet, the ultrasonic waveguide having an agitating member extending outward from the ultrasonic waveguide within the internal chamber of the housing intermediate the inlet and the outlet, the agitating member and the ultrasonic waveguide being constructed and arranged for dynamic motion of the agitating member relative to the ultrasonic waveguide upon ultrasonic vibration of the ultrasonic waveguide; and an excitation device operable to ultrasonically excite said ultrasonic waveguide and the agitating member; and an ultrasonic delivery device in fluid communication with the ultrasonic treatment device to receive liquid from the ultrasonic treatment device following treatment of the liquid by said treatment device, the ultrasonic delivery device comprising:

a housing having an internal chamber, an inlet for receiving liquid from the treatment device into the internal chamber of the delivery device housing and at least one exhaust port in fluid communication with the internal chamber of the delivery device housing whereby liquid within said internal chamber exits the delivery device housing at said at least one exhaust port;

an ultrasonic waveguide separate from the delivery device housing, said waveguide being disposed at least in part within the internal chamber of the delivery device housing to ultrasonically energize liquid within said internal chamber prior to said liquid being exhausted from said housing through the at least one exhaust port; and an excitation device operable to ultrasonically excite said ultrasonic waveguide of said delivery device.

2. The system set forth in claim 1 wherein the ultrasonic delivery device further comprises a valve member moveable relative to the housing between a closed position in which liquid within the internal chamber of said device is inhibited against exhaustion from the delivery device housing via the at least one exhaust port, and an open position in which liquid is exhaustable from the delivery device housing via the at least one exhaust port, the excitation device being operable in the open position of the valve member to ultrasonically excite said ultrasonic waveguide of said delivery device.

3. The system set forth in claim 1 wherein a plurality of agitating members extend outward from the ultrasonic waveguide of the treatment device in longitudinally spaced relationship with each other within the internal chamber of the treatment device housing.

4. The system set forth in claim 1 wherein the agitating member and ultrasonic waveguide of the ultrasonic treatment device are constructed and arranged to amplify the displacement of the agitating member relative to the displacement of the ultrasonic waveguide of said treatment device upon ultrasonic vibration of said ultrasonic waveguide.

5. The system set forth in claim 4 wherein the ultrasonic waveguide of the treatment device has a nodal region and an antinodal region, the agitating member extending transversely outward from said ultrasonic waveguide in the antinodal region.

6. The system set forth in claim 5 wherein the agitating member comprises a ring extending circumferentially around said ultrasonic waveguide.

7. The system set forth in claim 1 wherein the ultrasonic waveguide of the ultrasonic delivery device is generally tubular along at least a portion thereof, said tubular portion having a terminal end disposed within the internal chamber of the housing of said delivery device.

8. An ultrasonic liquid treatment and delivery system comprising:

an ultrasonic treatment device comprising:

a housing having an inlet for receiving liquid into the housing, an outlet through which liquid exits the treatment device housing, and an internal flow path in fluid communication with the inlet and the outlet to direct the flow of liquid within the housing from said inlet to said outlet;

an ultrasonic waveguide separate from the housing, said ultrasonic waveguide being elongate and disposed at least in part within the flow path to ultrasonically energize liquid within the flow path, the ultrasonic waveguide having an agitating member extending outward from the ultrasonic waveguide within the flow path, the agitating member and the ultrasonic waveguide being constructed and arranged for dynamic motion of the agitating member relative to the ultrasonic waveguide upon ultrasonic vibration of the ultrasonic waveguide; and an excitation device operable to ultrasonically excite said ultrasonic waveguide and the agitating member; and an ultrasonic delivery device in fluid communication with the ultrasonic treatment device to receive liquid from the ultrasonic treatment device following treatment of the liquid by said treatment device, the ultrasonic delivery device comprising:

a housing having an internal chamber, an inlet for receiving liquid from the treatment device into the internal chamber of the delivery device housing and at least one exhaust port in fluid communication with the internal chamber of the delivery device housing whereby liquid within said internal chamber exits the delivery device housing at said at least one exhaust port;

an ultrasonic waveguide separate from the delivery device housing, said waveguide being disposed at least in part within the internal chamber of the delivery device housing to ultrasonically energize liquid within said internal chamber prior to said liquid being exhausted from said housing through the at least one exhaust port; and an excitation device operable to ultrasonically excite said ultrasonic waveguide of said delivery device.

9. The system set forth in claim 8 wherein the ultrasonic delivery device further comprises a valve member moveable relative to the housing between a closed position in which liquid within the internal chamber of said device is inhibited against exhaustion from the delivery device housing via the at least one exhaust port, and an open position in which liquid is exhaustable from the delivery device housing via the at least one exhaust port, the excitation device of said delivery device being operable in the open position of the valve member to ultrasonically excite said ultrasonic waveguide of said delivery device.

10. The system set forth in claim 8 wherein a plurality of agitating members extend outward from the ultrasonic waveguide of the treatment device in longitudinally spaced relationship with each other within the internal chamber of the treatment device housing.

11. The system set forth in claim 8 wherein the agitating member and ultrasonic waveguide of the ultrasonic treatment device are constructed and arranged to amplify the displacement of the agitating member relative to the displacement of the ultrasonic waveguide of said treatment device upon ultrasonic vibration of said ultrasonic waveguide.

12. The system set forth in claim 11 wherein the ultrasonic waveguide of the treatment device has a nodal region and an antinodal region, the agitating member extending transversely outward from said ultrasonic waveguide in the antinodal region.

13. The system set forth in claim 12 wherein the agitating member comprises a ring extending circumferentially around said ultrasonic waveguide.

14. The system set forth in claim 8 wherein the ultrasonic waveguide of the ultrasonic delivery device is generally tubular along at least a portion thereof, said tubular portion having a terminal end disposed within the internal chamber of the housing of said delivery device.

15. A process for ultrasonically treating a liquid and delivering the liquid as a spray of liquid droplets, said process comprising:

directing the liquid to flow along a flow path over a first ultrasonic waveguide, said first ultrasonic waveguide having at least one agitating member extending outward therefrom and into the flow path for contact with the liquid flowing along said flow path;

ultrasonically exciting the first ultrasonic waveguide and said agitating member to agitate the liquid as the liquid flows over the ultrasonic waveguide and agitating member;

further directing the liquid to flow along said flow path over a second waveguide, said second waveguide having a terminal end adjacent an exit of said flow path such that liquid flowing along said flow path flows over the terminal end of the second waveguide prior to the liquid exiting the flow path;

ultrasonically exciting the second ultrasonic waveguide at least at said terminal end to ultrasonically energize the liquid just prior to the liquid exiting the flow path such that the liquid exits the flow path as a spray of liquid droplets;

wherein the first ultrasonic waveguide is disposed within a first housing having an internal chamber, an inlet to said chamber and an outlet from said chamber, said internal chamber defining a portion of said flow path from said inlet to said outlet, and the second ultrasonic waveguide is disposed within a second housing separate from the first housing and having an internal chamber, an inlet in fluid communication with the outlet of the first housing, and an outlet, the internal chamber of the second housing further defining said flow path such that the outlet of said second housing defines the flow path exit, the step of further directing the liquid to flow along said flow path over a second waveguide comprising directing liquid exiting the outlet of the first housing to the inlet of the second housing for flow through the internal chamber of said second housing.

16. The process set forth in claim 15 further comprising positioning a valve member in an open position to permit liquid to flow through the outlet of the second housing, the valve member being formed separately from the first and second ultrasonic waveguides.

17. The process set forth in claim 16 further comprising positioning the valve member in a closed position to close the outlet of the second housing, at least a portion of the valve member extending outward of the terminal end of the second waveguide when the valve member is in the closed position.

* * * * *